(12) United States Patent
Chabas et al.

(10) Patent No.: US 7,282,490 B2
(45) Date of Patent: Oct. 16, 2007

(54) OSTEOPONTIN-RELATED COMPOSITIONS AND METHODS

(75) Inventors: Dorothee Chabas, Paris (FR); Lawrence Steinman, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 191 days.

(21) Appl. No.: 10/495,893

(22) PCT Filed: Nov. 21, 2002

(86) PCT No.: PCT/US02/37466

§ 371 (c)(1),
(2), (4) Date: Dec. 17, 2004

(87) PCT Pub. No.: WO03/046135

PCT Pub. Date: Jun. 5, 2003

(65) Prior Publication Data

US 2005/0119204 A1    Jun. 2, 2005

Related U.S. Application Data

(60) Provisional application No. 60/332,071, filed on Nov. 21, 2001.

(51) Int. Cl.
*A61K 31/70* (2006.01)
*A01N 43/04* (2006.01)
*C12P 21/06* (2006.01)
*C12N 15/00* (2006.01)
*C12N 5/00* (2006.01)
*C12N 5/02* (2006.01)

(52) U.S. Cl. .................. 514/44; 424/44; 435/69.1; 435/320.1; 435/325; 435/455

(58) Field of Classification Search .................. None
See application file for complete search history.

(56) References Cited

U.S. PATENT DOCUMENTS 5,695,761 A    12/1997    Denhardt et al.

FOREIGN PATENT DOCUMENTS

| WO | WO 01/26679 A2 | 4/2001 |
| WO | WO 01/71358 A1 | 9/2001 |
| WO | WO 02/092122 A2 | 11/2002 |

OTHER PUBLICATIONS

Goncalves, Bioessays, 2005, 27: 506-517.*
Ashkar, S. et al., "Eta-1 (osteopontin): an early component of type-1 (cell-mediated) immunity," *Science*, 287:860-864 (Feb. 4, 2000).
Becker, K. et al., "Analysis of a sequenced cDNA library from multiple sclerosis lesions," *J. Neuroimmunol.*, 77(1):27-38 (Jul. 1997).
Bell, J. and Lathrop, G.M., "Multiple loci for multiple sclerosis," *Nat. Genet.*, 13(4):464-468 (Aug. 1996).
Brocke, S. et al., "Antibodies to CD44 and integrin $\alpha_4$, but not L-selectin, prevent central nervous system inflammation and experimental encephalomyelitis by blocking secondary leukocyte recruitment," *Pro.c Natl. Acad. Sci. U S A*, 96(12):6896-6901 (Jun. 8, 1999).
Chabas, D. et al., "The influence of the proinflammatory cytokine, osteopontin, on autoimmune demyelinating disease," *Science*, 294:1731-1735 (Nov. 23, 2001).
Choi, S.S. et al., "Construction of a gene expression profile of a human fetal liver by single-pass cDNA sequencing," *Mamm. Genome.*, 6(9):653-657 (Sep. 1995).
Denhardt, D. and Guo, X., "Osteopontin: a protein with diverse functions," *FASEB J.*, 7(15):1475-1482 (Dec. 1993).
Denhardt, D.T. et al., "Osteopontin ad a means to cope with environmental insults: regulation of inflammation, tissue remodeling, and cell survival," *J. Clin Invest.*, 107(9):1055-1061 (May 2001).
Ebers, G. et al., "A full genome search in multiple sclerosis," *Nat. Genet.*, 13(4):472-476 (Aug. 1996).
Fisher, L. et al., "Flexible structures of SIBLING proteins, bone sialoprotein, and osteopontin," *Biochem. Biophys. Res. Commun.*, 280(2):460-465 (Jan. 19, 2001).
Gijbels, K. et al., "Administration of neutralizing antibodies to interleukin-6 (IL-6) reduces experimental autoimmune encephalomyelitis and is associated with elevated levels of IL-6 bioactivity in central nervous system and circulation," *Mol. Med.*, 1(7):795-805 (Nov. 1995).
Haines, J. et al., "A complete genomic screen for multiple sclerosis underscores a role for the major histocompatability complex. The Multiple Sclerosis Genetics Group," *Nat. Genet.*, 13(4):469-71 (Aug. 1996).
Hwang, S.M. et al., "Osteopontin inhibits induction of nitric oxide synthase gene expression by inflammatory mediators in mouse kidney epithelial cells," *J. Biol. Chem.*, 269(1):711-715 (Jan. 7, 1994).
Karin, N. et al., "Short peptide-based tolerogens without self-antigenic or pathogenic activity reverse autoimmune disease," *J. Immunol.*, 160(10):5188-5194 (May 15, 1998).
Oldberg, A. et al., "Cloning and sequence analysis of rat bone sialoprotein (osteopontin) cDNA reveals an Arg-Gly-Asp cell-binding sequence," *Proc. Natl. Acad. Sci. USA*, 83(23):8819-8823 (Dec. 1986).

(Continued)

*Primary Examiner*—Sumesh Kaushal
*Assistant Examiner*—Kelaginamane T. Hiriyanna
(74) *Attorney, Agent, or Firm*—Townsend & Townsend and Crew LLP

(57) ABSTRACT

This invention provides a method for reducing the amount of osteopontin in an osteopontin-expressing cell comprising introducing into the cell a nucleic acid which specifically inhibits osteopontin expression in the cell. This invention also provides methods for inhibiting the onset of, and treating, osteopontin-related disorders, as well as compositions for practicing the same. This invention further provides methods for determining the amount of osteopontin in a sample, and a kit for practicing the same. This invention also provides methods for determining whether an agent reduces the amount of osteopontin in an osteopontin-expressing cell. Finally, this invention provides methods for treating a subject afflicted with a disorder mediated by an endogenous protein.

10 Claims, 7 Drawing Sheets

OTHER PUBLICATIONS

O'Regan, A.W. et al., "Osteopontin (Eta-1) in cell-mediated immunity: teaching an old dog new tricks," *Immunol. Today.*, 21(10):475-478 (Oct. 2000).

Pedotti, R. et al., "An unexpected version of horror autotoxicus: anaphylactic shock to a self-peptide," *Nat. Immunol.*, 2(3):216-222 (Mar. 2001).

Pitt, D. et al., "Glutamate excitotoxicity in a model of multiple sclerosis," *Nat. Med.*, 6(1):67-70 (Jan. 2000).

Rittling, S.R. and Denhardt, D.T., "Osteopontin function in pathology: lessons from osteopontin-deficient mice," *Exp. Nephrol.*, 7(2):103-113 (Mar.-Apr. 1999).

Rittling, S.R. et al., "Mice lacking osteopontin show normal development and bone structure but display altered osteoclast formation in vitro," *J. Bone Miner. Res.*, 13(7):1101-1111 (Jul. 1998).

Sasaki, N. et al. "Characterization of gene expression in mouse blastocyst using single-pass sequencing of 3995 clones," *Genomics*, 49(2):167-179 (Apr. 15, 1998).

Shin, S.L. et al., "Expression of osteopontin mRNA in the adult rat brain," *Neurosci. Lett.*, 273(2):73-76 (Oct. 1, 1999).

Sobel, R. et al., "Vitronectin and integrin vitronectin receptor localization in multiple sclerosis lesions," *J. Neuropathol. Exp. Neurol.*, 54(2):202-213 (Mar. 1995).

Steinman, L., "Immunotherapy of multiple sclerosis: the end of the beginning," *Current Opinion in Immunology*, 13:597-600 (2001).

Steinman, L., "Multiple sclerosis: a two-stage disease," *Nat. Immunology*, 2(9):762-764 (Sep. 2001).

Trapp, B. et al., "Axonal transection in the lesions of multiple sclerosis," *N. Engl. J. Med.*, 338(5):278-285 (Jan. 29, 1998).

Verma, I. and Nikunj, S., "Gene therapy—promises, problems and prospects," *Nature*, 389:239-242, Sep. 18, 1997.

Villarroya, H. et al., "Expression of TNFα in central neurons of Lewis rat spinal cord after EAE induction," *J. Neurosci. Res.*, 49(5):592-599 (Sep. 1, 1997).

Young, M. et al., "cDNA cloning, mRNA distribution and heterogeneity, chromosomal location, and RFLP analysis of human osteopontin (OPN)," *Genomics*, 7(4):491-502 (Aug. 1990).

* cited by examiner

FIGURES 4A-4D
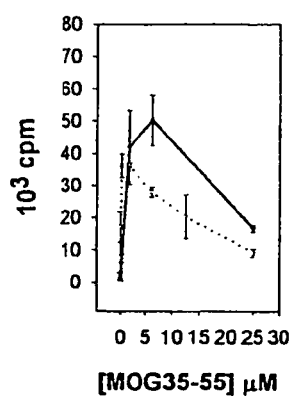
Fig 4A
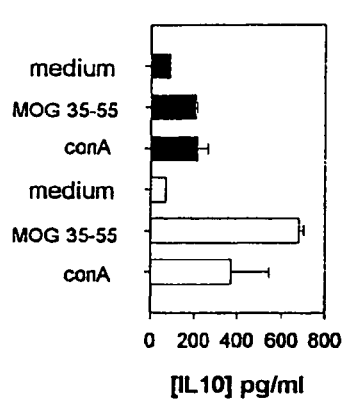
Fig 4B
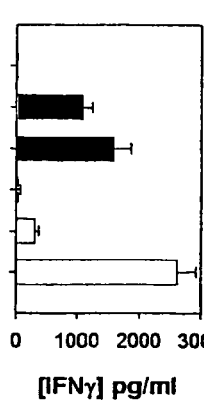
Fig 4C
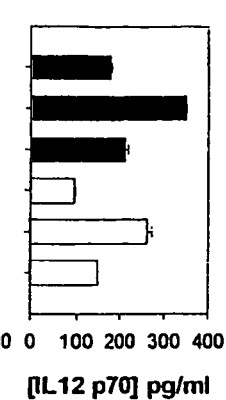
Fig 4D

OSTEOPONTIN-RELATED COMPOSITIONS AND METHODS

The invention disclosed herein was made with Government support under Grant No. R0118235 from the National Institutes of Health of the United States Department of Health and Human Services. Accordingly, the United States Government has certain rights in this invention.

CROSS-REFERENCE TO RELATED APPLICATION

The present application is a US national stage of PCT/US02/37466, filed Nov. 21, 2002, which claims the benefit of U.S. Ser. No. 60/332,071, filed Nov. 21, 2001, both of which are incorporated by reference for all purposes.

Throughout this application, various publications are referenced in parentheses. Full citations for these publications may be found listed at the end of the specification. The disclosures of these publications in their entireties are hereby incorporated by reference into this application in order to more fully describe the state of the art as known to those skilled therein.

FIELD OF THE INVENTION

This invention relates to treating and preventing osteopontin-related disorders such as multiple sclerosis, and quantitatively measuring osteopontin in a sample. This invention also relates to methods of using osteopontin in the treatment of disorders, such as autoimmune disorders, that are mediated by endogenous proteins.

BACKGROUND OF THE INVENTION

Multiple Sclerosis

Multiple sclerosis ("MS") is a demyelinating disease characterized by inflammation in the brain and spinal cord. MS is the most common human autoimmune disease involving the nervous system. In the United States, approximately 250,000 individuals suffer from MS. In MS, cells of the immune system invade and destroy myelin, the fatty material that insulates nerves in the brain and spinal cord. Other CNS cells produce a hardened sclerotic lesion (plaque) around the multiple demyelinated sites. Neurologic findings suggest lesions in separate areas of the CNS that occur at different times.

A typical presentation of MS involves an initial course, running for several years to more than a decade, manifest by episodes of relapse followed by remission. Relapses often follow an episode of a viral infection of the upper respiratory system or gastrointestinal tract. In about one third of MS patients, this disease evolves into a progressive course termed "secondary progressive MS." In a minority of patients, progressive neurologic deterioration without remission occurs from the onset of disease, and this is called "primary progressive MS." The pathophysiologic and genetic causes underlying primary versus secondary progressive MS remain unclear.

Clinical problems observed in MS patients may include disturbances in visual acuity, sometimes culminating in blindness; double vision; motor disturbances affecting walking and use of the hands; uncoordination; bowel and bladder incontinence; spasticity; and sensory disturbances including loss of touch, pain, temperature and proprioception. The pathology of MS lies entirely in the central nervous system and is characterized by a classic picture of inflammation surrounding venules and extending into the myelin sheath.

Immune responses to various components of the myelin sheath have been detected in MS patients. These components include myelin basic protein ("MBP"), proteolipid ("PLP"), transaldolase and 2',3' cyclic nucleotide 3'phosphodiesterases ("CNP"), as well as two members of the immunoglobulin supergene family found in the myelin sheath, i.e., myelin oligodendroglial glycoprotein ("MOG") and myelin-associated glycoprotein ("MAG") (11). In addition, some inducible heat shock proteins, including crystallin-B, can be detected in glial cells in MS lesions and can stimulate an immune response in MS patients. The major T and B cell response in the central nervous systems of the roughly two thirds of MS patients who are HLA DR2 is directed to a region between residues 84 and 103 of MBP (14, 18).

Osteopontin

Osteopontin ("OPN"), also called early T cell activation gene-1, is a human protein whose primary structure has been characterized (25). OPN is a pleiotropic protein having a conserved RGD binding motif, and when produced by osteoblasts is involved in the anchoring of osteoclasts to the mineral of bone matrix. Expression of osteopontin in bone tissue is stimulated by 1-alpha-1,25-dihydroxyvitamin D3. Osteopontin also provides the protein matrix for urinary stones.

Osteopontin also plays roles in inflammation and in immunity to infectious diseases (29). Osteopontin costimulates T cell proliferation (8), and is classified as a Th1 cytokine, due to its ability to enhance IFN-gamma and IL-12 production, and to diminish IL-10 (32). It has been shown that osteopontin expression in rat aortic smooth muscle cells is inhibited by NK-104, a 3-hydroxy-3-methylglutaryl coenzyme A reductase inhibitor.

SUMMARY OF THE INVENTION

The invention provides methods for preventing or treating a patient suffering or at risk of a disorder in which expression of osteopontin contributes to the pathogenesis. These methods comprise administering to the subject an effective amount of a nucleic acid comprising a segment encoding osteopontin, whereby the nucleic acid is expressed in the patient to produce osteopontin, and the osteopontin induces an immune response that reduces the level of osteopontin in the patient. In some methods, the immune response includes formation of antibodies. In some methods, the patient is suffering from or at risk of raft versus host disease, epilepsy, a granulomatous disorder, herpes simplex keratisits, bacterial arthritis, or an autoimmune disease. Examples of autoimmune diseases include multiple sclerosis, rheumatoid arthritis, type I diabetes.

The nucleic acid can be DNA, in which case the nucleic acid further comprises a promoter and optionally an enhancer in operable linkage to the segment encoding the osteopontin. The promoter can be constitutive or cell-type specific. Alternatively, the nucleic acid can be RNA. In some methods, the nucleic acid is administered intramuscularly. In some methods, the the subject is a human.

Some methods, further comprise monitoring a decrease in the level of osteopontin responsive to the administering step. In some methods, the level of osteopontin is monitored in a cell of the patient selected from the group consisting of a neuron, a macrophage, a vascular endothelial cell, an astrocyte and a microglial cell. In some methods, the patient has the disorder and the method further comprises monitoring a decrease in the symptoms of the patient responsive to the administering.

The invention further provides a composition comprising a nucleic acid encoding osteopontin and a pharmaceutically acceptable carrier.

The invention further provides methods for preventing or treating a patient suffering from or at risk of a disorder in which expression of osteopontin contributes to the pathogenesis. These methods comprise administering to the patient an effective amount of osteopontin, whereby the osteopontin induces an immune response that reduces the level of osteopontin in the patient. In some such methods, the the osteoponin is administered with an adjuvant. In some methods, the immune response comprises formation of antibodies to osteopontin.

In some methods, the patient is suffering from or at risk of graft versus host disease, epilepsy, a granulomatous disorder, herpes simplex keratisits, bacterial arthritis or an autoimmune disease as described above. In some methods the patient is a human.

Some methods further comprise monitoring a decrease in the level of osteopontin responsive to the administering step. In some methods, the level of osteopontin is monitored in a cell of the patient selected from the group consisting of a neuron, a macrophage, a vascular endothelial cell, an astrocyte and a microglial cell. In some methods, the the patient has the disease and the method further comprises monitoring a decrease in the symptoms of the patient responsive to the administering.

The invention further provides a composition comprising osteoponin and an adjuvant.

This invention provides a method for reducing the amount of osteopontin in disorders in which osteopontin is produced.

This invention also provides a first method for inhibiting the onset of an osteopontin-related disorder in a subject comprising administering to the subject a prophylactically effective amount of a nucleic acid which specifically reduces levels of osteopontin.

In addition, this invention provides a first method for treating a subject afflicted with an osteopontin-related disorder in a subject comprising administering to the subject a therapeutically effective amount of a nucleic acid which specifically inhibits the expression of osteopontin in the subject's osteopontin-expressing cells.

This invention further provides a second method for inhibiting the onset of an osteopontin-related disorder in a subject comprising administering to the subject a prophylactically effective amount of an anti-osteopontin antibody or antigen-binding portion thereof.

This invention further provides a second method for treating a subject afflicted with an osteopontin-mediated disorder comprising administering to the subject a therapeutically effective amount of an anti-osteopontin antibody or antigen-binding portion thereof.

This invention further provides two compositions. The first composition comprises a nucleic acid which specifically inhibits the expression of osteopontin in an osteopontin-expressing cell and a pharmaceutically acceptable carrier. The second composition comprises an anti-osteopontin antibody or antigen-binding portion thereof and a pharmaceutically acceptable carrier.

This invention further provides a first method for determining the amount of osteopontin in a sample comprising (a) contacting the sample with an anti-osteopontin antibody or antigen-binding portion thereof under suitable conditions, (b) determining the amount of antibody or antigen-binding portion thereof bound to the sample, and (c) comparing the amount so determined to a known standard, thereby determining the amount of osteopontin in the sample.

This invention further provides a second method for determining the amount of osteopontin in a sample comprising (a) contacting the sample under suitable conditions with a nucleic acid which specifically hybridizes to osteopontin-encoding mRNA, (b) determining the amount of nucleic acid so hybridized, (c) comparing the amount of nucleic acid so determined to a known standard so as to determine the amount of osteopontin-encoding mRNA in the sample, and (d) comparing the amount of mRNA so determined to a known standard, thereby determining the amount of osteopontin in the sample.

This invention provides a kit for practicing the first and second quantitative methods comprising (a) an agent selected from the group consisting of (i) an anti-osteopontin antibody or antigen-binding portion thereof and (ii) a nucleic acid which specifically hybridizes with osteopontin-encoding mRNA, and (b) instructions for use.

This invention also provides two methods ("assays") for determining whether an agent reduces the amount of osteopontin in an osteopontin-expressing cell. The first assay comprises (a) contacting the cell with the agent under suitable conditions, (b) determining the amount of osteopontin in the cell, and (c) comparing the amount so determined to the amount of osteopontin in a comparable cell in the absence of the agent, thereby determining whether the agent reduces the amount of osteopontin in the cell.

The second assay comprises the steps of (a) contacting the agent with osteopontin under suitable conditions, (b) determining the activity of osteopontin in the presence of the agent, and (c) comparing the activity so determined to the activity of osteopontin in the absence of the agent, thereby determining whether the agent reduces the activity of osteopontin.

This invention further provides a method of treating a subject afflicted with multiple sclerosis comprising administering to the subject a therapeutically effective amount of an expressible nucleic acid encoding osteopontin. Also provided is a method of inhibiting the onset of multiple sclerosis in a subject comprising administering to the subject a prophylactically effective amount of an expressible nucleic acid encoding osteopontin.

This invention further provides kits for treating or preventing an osteopontin-related disorder. The first kit comprises a nucleic acid which specifically inhibits the expression of osteopontin in an osteopontin-expressing cell, and instructions for using the nucleic acid in the treatment or prophylaxis of an osteopontin-related disorder. The second kit comprises an anti-osteopontin antibody or antigen-binding portion thereof, and instructions for using the antibody or antigen-binding portion thereof in the treatment or prophylaxis of an osteopontin-related disorder.

Finally, this invention provides two methods for treating a subject afflicted with a disorder mediated by an endogenous protein. The first method comprises administering to the subject (a) osteopontin and (b) the endogenous protein or an antigenic portion thereof, wherein the osteopontin and endogenous protein or antigenic portion thereof are administered in amounts effective to treat the subject. The second method for treating a subject afflicted with a disorder mediated by an endogenous protein comprises administering to the subject (a) an expressible osteopontin-encoding nucleic acid and (b) an expressible nucleic acid encoding the endogenous protein or an antigenic portion thereof, wherein the nucleic acids are administered in amounts effective to treat the subject.

BRIEF DESCRIPTION OF THE DRAWINGS

In FIG. 2C, OPN was broadly expressed in CNS microglia, especially near inflammatory lesions, but not in adjacent peripheral nerves (arrow). In FIG. 2D, expression in neurons (arrows) was detectable during the acute phase (N=4) and relapse (N=2), but not during remission (N=1) or in mice with inflammatory lesions which never developed paralysis (N=2). OPN expression in astrocytes (arrows) (FIG. 2E) and choroid plexus cells (FIG. 2F) was also more frequent and more pronounced in immunized mice (100%) than in controls (25%).

FIGS. 3A-3C These Figures relate to clinical attenuation of EAE in OPN−/− mice. OPN+/+ and OPN−/− mice are 129/C57BL/6 mixed background, maintained as a partially outbred strain (30). EAE was induced in OPN+/+ (N=18) (closed circles) and OPN−/− (N=17) (open circles) mice (30) with MOG 35-55, as described (31). EAE was scored as follows: 0=normal; 1=monoparesis; 2=paraparesis; 3=paraplegia; 4=Tetraparesis; and 5=moribund or dead. For each animal, a remission was defined by a decrease of the score of at least one point for at least two consecutive days. EAE was considered remitting when at least one remission occurred within the first 26 days, and progressive when no remission occurred.

In FIG. 3A, OPN−/− (open circles) mice have milder disease than OPN+/+ controls (closed circles). The error bars represent the standard error for each point. EAE was observed in 100% of both OPN+/+ and OPN−/− mice with MOG 35-55, [N=18 for OPN+/+ and N=17 for OPN−/−]. Although EAE could be induced with a 100% incidence in OPN−/− mice, a significantly reduced severity of disease developed in the OPN−/− group, with a decrease of the mean EAE score (at day 30, mean EAE score 2.5 in OPN+/+, compared with 1.2 in OPN−/−, Mann-Whitney Rank Sum test p=0.0373) and a decrease of the mean maximum severity score (mean severity 3.7 in OPN+/+, compared to 2.8 in OPN−/−, Mann-Whitney Rank Sum test p=0.0422). There was no significant delay of the day of disease onset (mean 11.7 days in OPN+/+, compared to 12.5 days in OPN−/−, Mann-Whitney Rank Sum test p=0.322).

In FIG. 3B, OPN−/− mice (open circles) are protected from EAE-related death, with no mice dead out of 17, as compared with 7 dead out of 18 among the OPN+/+ mice at day 70 (p=0.0076 by Fisher's exact test).

FIG. 3C shows that OPN promotes progressive EAE. The bars represent the percentage of mice having a remitting (black) or progressive (white) disease in each group. OPN−/− mice showed a distinct evolution of EAE, with a much higher percentage of mice having remissions compared to the controls. (10 out of 18 had remissions in the OPN+/+ group (55.5%), compared to 16 out of 17 in the OPN−/− group (94.1%), p=0.0178 by Fisher's exact test).

FIG. 4A This Figure shows inhibition of T cell proliferation in OPN−/− mice. A proliferation assay was performed on draining lymph nodes (LN) from OPN+/+ (closed circles) and OPN−/− (open circles) mice (30), 14 days after induction of EAE. EAE was induced with MOG 35-55, as described (31). Draining LN were removed 14 days after immunization, and LN cells were stimulated in 96-well flat bottom plates (2.5 10$^6$/ml, 200 ml/well) with serial dilutions of HPLC-purified MOG 35-55 (0-50 mM), as described (39). The medium contained 2% serum from the type of mouse tested, in order to avoid introducing OPN into the in vitro assays on OPN−/− cells. OPN+/+ normal mouse serum was used for the assays on OPN+/+ cells, while OPN−/− normal mouse serum was used for the assays on OPN−/− cells. Concanvalin A (2 mg/ml), a non-specific mitogen for T cells, was used as a non-specific positive control. [$^3$H] thymidine was added to the triplicates [mean±standard deviation graphed], after 72 h of antigen stimulation and its incorporation by the proliferating cells (in cpm) was measured 24 h later.

FIG. 4B This Figure shows that OPN−/− cells produce more IL-10 than OPN+/+ cells. OPN+/+ (black bars) and OPN−/− (white bars) LN cells were stimulated in the same way as for the proliferation assay (FIG. 4A), but in 24-well flat bottom plates (2 ml/well). MOG 35-55 was used at a concentration of 12.5 mM. IL-10 was measured by ELISA on the 48 h supernatants (dilution 1/2), in duplicate [mean±standard deviation graphed], according to the manufacturer's instructions (OPTEIA kit, PharMingen, San Diego, Calif.).

FIG. 4C This Figure shows that OPN−/− cells produce less IFN-gamma than OPN+/+ cells. OPN+/+ (filled bars) and OPN−/− (open bars) spleen cells were removed 14 days after induction of EAE with MOG 35-55 and stimulated as described in FIG. 4B, but with 4.5 $10^6$ cells/well. IFN-gamma was measured by ELISA on the 48 h supernatants (dilution 1/5), in triplicate, according to the manufacturer's instructions (OPTEIA kit, PharMingen, San Diego, Calif.).

FIG. 4D This Figure shows that OPN−/− cells produce less IL-12 than OPN+/+ cells. OPN+/+ (black bars) and OPN−/− (white bars) spleen cells were removed as described for FIG. 4C. IL-12 p70 was measured by ELISA on the 24 h supernatants (dilution 1/1), in duplicate [mean±standard deviation graphed], according to the manufacturer's instructions (OPTEIA kit, PharMingen, San Diego, Calif.).

DETAILED DESCRIPTION

Definitions

Figures 1A, 1B, 1C:
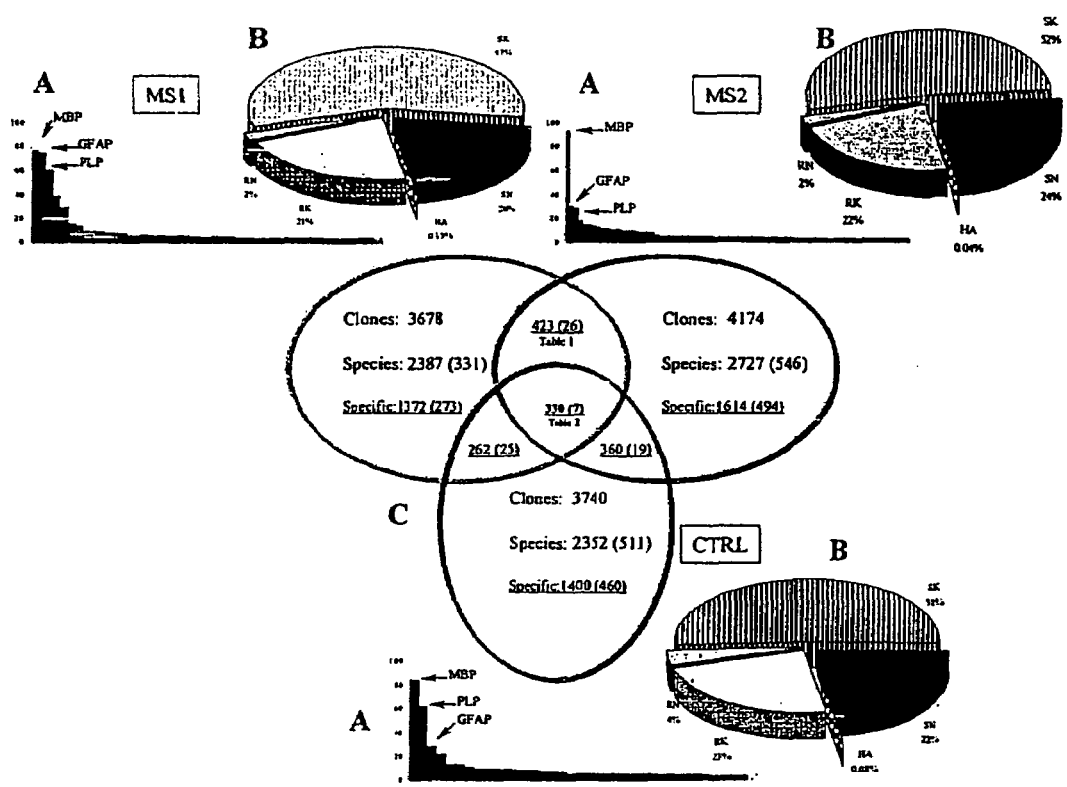
FIG. 1A Frequency distribution. Clones with a count higher than 6 were organized in decreasing order according to their frequency. Arrows indicate the three most common ESTs in each library. MBP was the most highly expressed gene in all three libraries. GFAP and PLP were the next most abundant species in the MS libraries, but their frequency order was reversed in the control library. Unidentified ESTs are shown in lighter color than known, annotated clones.
FIG. 1B Category distribution. Clones were distributed into one of the following categories: RN, redundant novel; RK, redundant known; HA, high abundance; SN, solitary novel; and SK, solitary known. The relative contribution to each category is shown in a pie chart for all libraries.
FIG. 1C Intersectional queries. All possible comparisons were performed among the three libraries. Clones were counted and distributed into their corresponding intersection on the Venn diagrams. The total number of sequenced clones is shown for each library. The number of different mRNA species for each library is also shown along with the number of unknown genes in parentheses. The number of RNA species that were specific for each library or intersection of libraries is displayed underlined, along with the number of unknown genes in parentheses.

"Activity" of osteopontin shall mean any enzymatic or binding function performed by that protein. Osteopontin activity includes, for example, binding to CD44.

"Antibody" shall include, by way of example, both naturally occurring and non-naturally occurring antibodies. Specifically, this term includes polyclonal and monoclonal antibodies, and fragments thereof. Furthermore, this term includes chimeric antibodies and wholly synthetic antibodies, and fragments thereof.

"Anti-sense nucleic acid" shall mean any nucleic acid which, when introduced into a cell, specifically hybridizes to at least a portion of an mRNA in the cell encoding a protein ("target protein") whose expression is to be inhibited, and thereby inhibits the target protein's expression.

"Catalytic nucleic acid" shall mean a nucleic acid that specifically recognizes a distinct substrate and catalyzes the chemical modification of this substrate.

"Comparable cell" shall mean a cell whose type is identical to that of another cell to which it is compared. Examples of comparable cells are cells from the same cell line.

"DNAzyme" shall mean a catalytic nucleic acid that is DNA or whose catalytic component is DNA, and which specifically recognizes and cleaves a distinct target nucleic acid sequence, which can be either DNA or RNA. Each DNAzyme has a catalytic component (also referred to as a "catalytic domain") and a target sequence-binding component consisting of two binding domains, one on either side of the catalytic domain.

"Endogenous protein" shall mean, with respect to a particular subject, a protein originally encoded by the subject's own genome.

"Expressible nucleic acid" shall mean a nucleic acid encoding a nucleic acid of interest and/or a protein of interest, which nucleic acid is an expression vector, plasmid or other construct which, when placed in a cell, permits the expression of the nucleic acid or protein of interest. Expression vectors and plasmids are well known in the art.

"Inhibiting" the onset of a disorder shall mean either lessening the likelihood of the disorder's onset, or preventing the onset of the disorder entirely. In the preferred embodiment, inhibiting the onset of a disorder means preventing its onset entirely.

"Inhibiting" the expression of a gene in a cell shall mean either lessening the degree to which the gene is expressed, or preventing such expression entirely.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Osteopontin" shall mean the human protein encoded by the mRNA sequence set forth in GenBank Accession No. J04765, all naturally occurring variants and homologues thereof, and where applicable herein, all antigenic fragments thereof.

Active fragments of osteopontin share a functional or binding property with full length osteopontin.

Epitopic fragments of osteopontin bind to a monoclonal antibody that binds to full length osteopontin.

"Osteopontin-related disorder" shall mean any disorder (a) characterized by the over-expression of osteopontin in an afflicted subject, (b) ameliorated by inhibiting osteopontin expression in an afflicted subject, and/or (c) ameliorated by inhibiting osteopontin activity in an afflicted subject, (d) in which expression of osteopontin contributes to the pathogenesis Expression of osteopontin that is normal in some individuals may nevertheless contribute toward an osteopontin-related disorder in other individuals if such other individuals the osteopontin acts in combinations with another cellular component, such as a protein, in pathogenesis. Some osteopontin-related disorders are characterized by an elevated Th1 immune response and a depressed Th2 immune response relative to the mean of such responses in a population of normal individuals (i.e., free of an osteopontin-related disease and not at risk of such a disease).

Over-expression of osteopontin means an expression level that is greater than the mean plus one standard deviation of that in a population of normal individuals. Preferably the expression level is at least ten times the mean of that in a population of normal individuals.

"Ribozyme" shall mean a catalytic nucleic acid molecule which is RNA or whose catalytic component is RNA, and which specifically recognizes and cleaves a distinct target nucleic acid sequence, which can be either DNA or RNA. Each ribozyme has a catalytic component (also referred to as a "catalytic domain") and a target sequence-binding component consisting of two binding domains, one on either side of the catalytic domain.

"Specifically hybridize" to a nucleic acid shall mean, with respect to a first nucleic acid, that the first nucleic acid hybridizes to a second nucleic acid with greater affinity than to any other nucleic acid.

"Specifically inhibit" the expression of a protein shall mean to inhibit that protein's expression (a) more than the expression of any other protein, or (b) more than the expression of all but 10 or fewer other proteins.

"Subject" or "patient" shall mean any animal, such as a human, non-human primate, mouse, rat, guinea pig or rabbit.

"Suitable conditions" shall have a meaning dependent on the context in which this term is used. That is, when used in connection with an antibody, the term shall mean conditions that permit an antibody to bind to its corresponding antigen. When this term is used in connection with nucleic acid hybridization, the term shall mean conditions that permit a nucleic acid of at least 15 nucleotides in length to hybridize to a nucleic acid having a sequence complementary thereto. When used in connection with contacting an agent to a cell, this term shall mean conditions that permit an agent capable of doing so to enter a cell and perform its intended function. In one embodiment, the term "suitable conditions" as used herein means physiological conditions.

"Treating" a disorder shall mean slowing, stopping or reversing the disorder's progression. In the preferred embodiment, treating a disorder means reversing the disorder's progression, ideally to the point of eliminating the disorder itself. As used herein, ameliorating a disorder and treating a disorder are equivalent.

The term "immune" response is the development of a beneficial humoral (antibody mediated) and/or a cellular (mediated by antigen-specific T cells or their secretion products) response directed against osteopontin an amyloid peptide in a recipient patient. Such a response can be an active response induced by An "immunogen" is capable of inducing an immunological response against itself on administration to a mammal, optionally in conjunction with an adjuvant.

The term "naked polynucleotide" refers to a polynucleotide not complexed with colloidal materials. Naked polynucleotides are sometimes cloned in a plasmid vector.

The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

Unless otherwise apparent from the context, all elements, steps or features of the invention can be used in any combination with other elements, steps or features.

General

This invention provides a method for reducing the amount of osteopontin in an osteopontin-expressing cell comprising introducing into the cell a nucleic acid which specifically inhibits osteopontin expression in the cell. In one embodiment, this method further reduces the amount of osteopontin secreted by an osteopontin-secreting cell.

In this method, the nucleic acid can be, for example, DNA or RNA. In the preferred embodiment, the nucleic acid is DNA.

In addition, the nucleic acid can be an anti-sense nucleic acid that hybridizes to osteopontin-encoding mRNA, or a catalytic nucleic acid that cleaves osteopontin-encoding mRNA. In the preferred embodiment, the nucleic acid is an expressible nucleic acid encoding an anti-sense nucleic acid that hybridizes to osteopontin-encoding mRNA, and/or encoding a catalytic nucleic acid that cleaves osteopontin-encoding mRNA.

Osteoponin expression can also be inhibited using zinc finger proteins or nucleic acids encoding the same as described in WO 00/00409. Alternatively, inhibition of expression can be achieved using siRNAs as described by WO 99/32619, Elbashir, EMBO J. 20, 6877-6888 (2001) and Nykanen et al., Cell 107, 309-321 (2001); WO 01/29058.

In these methods, the osteopontin-expressing cell can be, for-example, a neuron, a macrophage, a vascular endothelial cell, an astrocyte or a microglial cell. In the preferred embodiment, the cell is a neuron.

This invention also provides a first method for inhibiting the onset of an osteopontin-related disorder in a subject comprising administering to the subject a prophylactically effective amount of a nucleic acid which specifically inhibits the expression of osteopontin in the subject's osteopontin-expressing cells.

In addition, this invention provides a first method for treating a subject afflicted with an osteopontin-related disorder in a subject comprising administering to the subject a therapeutically effective amount of a nucleic acid which specifically inhibits the expression of osteopontin in the subject's osteopontin-expressing cells.

In these first methods of prophylaxis and treatment, the nucleic acid can be, for example, DNA or RNA. In the preferred embodiment, the nucleic acid is DNA.

In addition, the nucleic acid can be an anti-sense nucleic acid that hybridizes to osteopontin-encoding mRNA, or a catalytic nucleic acid that cleaves osteopontin-encoding mRNA. In the preferred embodiment, the nucleic acid is an expressible nucleic acid encoding an anti-sense nucleic acid that hybridizes to osteopontin-encoding mRNA, and/or encoding a catalytic nucleic acid that cleaves osteopontin-encoding mRNA.

Also in these first methods of prophylaxis and treatment, the subject's cells in which the amount of osteopontin is reduced can be, for example, neurons, macrophages, vascular endothelial cells, astrocytes or microglial cells.

This invention further provides a second method for inhibiting the onset of an osteopontin-related disorder in a subject comprising administering to the subject a prophylactically effective amount of an anti-osteopontin antibody or antigen-binding portion thereof.

This invention further provides a second method for treating a subject afflicted with an osteopontin-mediated disorder comprising administering to the subject a therapeutically effective amount of an anti-osteopontin antibody or antigen-binding portion thereof.

In the preferred embodiment of the first and second methods of prophylaxis and treatment, the osteopontin-related disorder is multiple sclerosis. Preferably, the subject is a human.

This invention further provides two compositions. The first composition comprises a nucleic acid which specifically inhibits the expression of osteopontin in an osteopontin-expressing cell and a pharmaceutically acceptable carrier. The second composition comprising an anti-osteopontin antibody or antigen-binding portion thereof and a pharmaceutically acceptable carrier.

Determining a therapeutically or prophylactically effective amount of the instant compositions can be done based on animal data using routine computational methods. In one embodiment, the therapeutically or prophylactically effective amount contains between about 0.1 mg and about 1 g of nucleic acid or protein, as applicable. In another embodiment, the effective amount contains between about 1 mg and about 100 mg of nucleic acid or protein, as applicable. In a further embodiment, the effective amount contains between about 10 mg and about 50 mg of the nucleic acid or protein, as applicable.

In this invention, administering the instant compositions can be effected or performed using any of the various methods and delivery systems known to those skilled in the art. The administering can be performed, for example, intravenously, orally, via implant, transmucosally, transdermally, intramuscularly, intrathecally, and subcutaneously. The following delivery systems, which employ a number of routinely used pharmaceutical carriers, are only representative of the many embodiments envisioned for administering the instant compositions.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone. Osteopontin or nucleic acids of the invention can also be administered attached to particles using a gene gun.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

This invention further provides a first method for determining the amount of osteopontin in a sample comprising (a) contacting the sample with an anti-osteopontin antibody or antigen-binding portion thereof under suitable conditions, (b) determining the amount of antibody or antigen-binding portion thereof bound to the sample, and (c) comparing the amount so determined to a known standard, thereby determining the amount of osteopontin in the sample.

In one embodiment of this first quantitative method, the agent is an anti-osteopontin antibody or antigen-binding portion thereof. Preferably, the antibody or antigen-binding portion thereof is labeled with a detectable marker.

This invention further provides a second method for determining the amount of osteopontin in a sample comprising (a) contacting the sample under suitable conditions with a nucleic acid which specifically hybridizes to osteopontin-encoding mRNA, (b) determining the amount of nucleic acid so hybridized, (c) comparing the amount of nucleic acid so determined to a known standard so as to determine the amount of osteopontin-encoding mRNA in the sample, and (d) comparing the amount of mRNA so determined to a known standard, thereby determining the amount of osteopontin in the sample.

In one embodiment of this second quantitative method, the nucleic acid is labeled with a detectable marker.

In the first and second quantitative methods, the sample can be any sample containing or suspected of containing osteopontin alone, or in the presence of osteopontin-producing cells. In one embodiment, the sample is a tissue sample. Tissue samples include, without limitation, bodily fluid samples such as cerebrospinal fluid and blood and its component parts, and sections of solid tissue such as brain and spinal cord. Tissue samples can comprise, for example, neurons, macrophages, vascular endothelial cells, astrocytes or microglial cells. In one embodiment, the tissue sample is from a subject afflicted with or suspected of being afflicted with an osteopontin-related disorder, preferably multiple sclerosis.

In a further embodiment, the first and second quantitative methods comprise the step of determining the location of osteopontin within the tissue sample. Steps (a) and (b) of these methods can be performed, for example, either in vivo or ex vivo.

This invention provides a kit for practicing the first and second quantitative methods comprising (a) an agent selected from the group consisting of (i) an anti-osteopontin antibody or antigen-binding portion thereof and (ii) a nucleic acid which specifically hybridizes with osteopontin-encoding mRNA, and (b) instructions for use.

This invention also provides two methods ("assays") for determining whether an agent reduces osteopontin activity or the amount of osteopontin in an osteopontin-expressing cell. The first assay comprises (a) contacting the cell with the agent under suitable conditions, (b) determining the amount of osteopontin in the cell, and (c) comparing the amount so determined to the amount of osteopontin in a comparable cell in the absence of the agent, thereby determining whether the agent reduces the amount of osteopontin in the cell.

In the first assay, the osteopontin-expressing cell can be, for example, a neuron, a macrophage, a vascular endothelial cell, an astrocyte and a microglial cell. Preferably, the cell is a human cell. In step (b) of the first assay, the amount of osteopontin in the cell is determined using an anti-osteopontin antibody or antigen-binding portion thereof. Alternatively, in step (b), the amount of osteopontin in the cell is determined using a nucleic acid which specifically hybridizes with osteopontin-encoding mRNA.

The second assay comprises the steps of (a) contacting the agent with osteopontin under suitable conditions, (b) determining the activity of osteopontin in the presence of the agent, and (c) comparing the activity so determined to the activity of osteopontin in the absence of the agent, thereby determining whether the agent reduces the activity of osteopontin.

In one embodiment of the second assay, the osteopontin is in a cell. This cell can be, for example, a neuron, a macrophage, a vascular endothelial cell, an astrocyte and a microglial cell. Preferably, the cell is a human cell.

This invention further provides methods for treating a subject afflicted with a disorder mediated by an endogenous protein. One method comprises administering to the subject (a) osteopontin and (b) the endogenous protein or an antigenic portion thereof, wherein the osteopontin and endogenous protein or antigenic portion thereof are administered in amounts effective to treat the subject.

In this method, the osteopontin and endogenous protein or antigenic portion thereof can be administered simultaneously. Alternatively, the osteopontin and endogenous protein or antigenic portion thereof are administered separately.

A second method for treating a subject afflicted with a disorder mediated by an endogenous protein comprises administering to the subject (a) an expressible osteopontin-encoding nucleic acid and (b) an expressible nucleic acid encoding the endogenous protein or an antigenic portion thereof, wherein the nucleic acids are administered in amounts effective to treat the subject.

In this second method, the osteopontin-encoding nucleic acid and nucleic acid encoding the endogenous protein or antigenic portion thereof can be administered simultaneously, either on the same vector or separate vectors. Alternatively, the osteopontin-encoding nucleic acid and nucleic acid encoding the endogenous protein or antigenic portion thereof are administered separately.

In one embodiment of the first and second methods for treating a subject afflicted with a disorder mediated by an endogenous protein, the disorder is an autoimmune disorder. In another embodiment, the disorder is multiple sclerosis, insulin-dependent diabetes mellitus, rheumatoid arthritis, autoimmune uveitis, primary billiary cirrhosis or Alzheimer's disease. Preferably, the disorder is multiple sclerosis.

In the first and second methods where the disorder treated is multiple sclerosis, the endogenous protein can be, for example, myelin basic protein, proteolipid protein, myelin-associated glycoprotein, cyclic nucleotide phosphodiesterase, myelin-associated oligodendrocytic basic protein, or alpha-B-crystalin.

Table 1 sets forth examples of disorders treatable by the instant methods, and their corresponding endogenous proteins.

TABLE 1

Human Endogenous Protein-Mediated Disorders

| Autoimmune Disease | Tissue Targeted | Self-Protein(s) Associated With An Autoimmune Disease |
|---|---|---|
| Multiple sclerosis | central nervous system | myelin basic protein, proteolipid protein, myelin associated glycoprotein, cyclic nucleotide phosphodiesterase, yelin-associated glycoprotein, myelin-associated oligodendrocytic basic protein; alpha-B-crystalin |
| Guillian Barre Syndrome | peripheral nerv. sys. | peripheral myelin protein I and others |
| Insulin Dependent Diabetes Mellitus | ☐ cells in islets of pancreas | tyrosine phosphatase IA2, IA-2b; glutamic acid decarboxylase (65 and 67 kDa forms), carboxypeptidase H, insulin, proinsulin, heat shock proteins, glima 38, islet cell antigen 69 KDa, p52, ganglioside antigens, islet cell glucose transporter GLUT-2 |
| Rheumatoid Arthritis | synovial joints | Immunoglobulin, fibrin, filaggrin, type I, II, III, IV, V, IX, and XI collagens, GP-39, hnRNPs |
| Autoimmune Uveitis | eye, uvea | S-antigen, interphotoreceptor retinoid binding protein (IRBP), rhodopsin, recoverin |
| Primary Biliary Cirrhosis | biliary tree of liver | pyruvate dehydrogenase complexes (2-oxoacid dehydrogenase) |
| Autoimmune Hepatitis | Liver | Hepatocyte antigens, cytochrome P450 |
| Pemphigus vulgaris | Skin | Desmoglein-1, −3, and others |
| Myasthenia Gravis | nerve-muscle junct. | acetylcholine receptor |
| Autoimmune gastritis | stomach/parietal cells | H$^+$/K$^+$ ATPase, intrinsic factor |
| Pernicious Anemia | Stomach | intrinsic factor |
| Polymyositis | Muscle | histidyl tRNA synthetase, other synthetases, other nuclear antigens |
| Autoimmune Thyroiditis | Thyroid | Thyroglobulin, thyroid peroxidase |
| Graves's Disease | Thyroid | Thyroid-stimulating hormone receptor |
| Vitiligo | Skin | Tyrosinase, tyrosinase-related protein-2 |
| Systemic Lupus Eryth. | Systemic | nuclear antigens: DNA, histones, ribonucleoproteins |
| Celiac Disease | Small bowel | Transglutaminase |

| Neurodegenerative Disease | Pathologic Deformity | Endogenous Protein |
|---|---|---|
| Alzherimer's disease | senile plaques | amyloid ☐ protein |
| Parkinson's disease | Lewy bodies | ☐-synuclein |

TABLE 1-continued

| Human Endogenous Protein-Mediated Disorders | | |
|---|---|---|
| Huntington's disease | intranuclear inclusions | Huntingtin protein |
| Prion disease | Prion protein inclusions | Prion protein |

| Disease | Abnormality | Endogenous Proteins Associated With Disease |
|---|---|---|
| Obesity | weight gain due to energy intake > expenditure | syndecan-3, perilipin, Orexin, Galanin, glucogon-like peptide receptor, |
| Osteoarthritis | cartilage degeneration | cathepsins, plasmin, collagenases, metalloproteinases |
| Spinal cord injury | inhibition of regeneration | Nogo-1 |
| Hypertension | persistent high blood pressure | angiotensin-converting enzyme |
| Peptic ulcer disease | excess stomach acid | $H^+/K^+$ ATPase, gastrin |
| Aging | | superoxide dismutase |
| Depression | excessive serotonin | serotonin 5HT2 receptor, $\square_1$-adrenergic receptor |
| Gout | Excess uric acid | Xanthine oxidase |
| Migraine headaches | vasospasm | serotonin $5HT_{1B}$ and $5HT_{1D}$ receptors |
| Hyperlipidemia | elevated lipids | HMG CoA-reductase, apolipoproteins A, B-100 |
| Coronary artery disease | obstruction of coronary arteries restricting blood flow | Angiotensin-converting enzyme, apolipoproteins A, B-100 |

Finally, this invention provides kits for treating or preventing an osteopontin-related disorder. The first kit comprises a nucleic acid which specifically inhibits the expression of osteopontin in an osteopontin-expressing cell, and instructions for using the nucleic acid in the treatment or prophylaxis of an osteopontin-related disorder. The second kit comprises an anti-osteopontin antibody or antigen-binding portion thereof, and instructions for using the antibody or antigen-binding portion thereof in the treatment or prophylaxis of an osteopontin-related disorder.

Methods of Treatment Using Osteoponin or Nucleic Acids Encoding Osteononin

The invention provides methods of treating osteopontin related disorders using osteopontin, epitopic fragments thereof or nucleic acids encoding either of these, graft versus host disease. These methods are useful for treating a variety of disease for which downregulation of type 1 immune response and or upregulation of type 2 immune response is required. Such diseases include autoimmune diseases, host versus graft disease and graft versus host disease, granulomatous disorder, herpes simplex keratisis, bacterial arthritis and epilepsy. Autoimmune diseases include multiple sclerosis, rheumatoid arthritis, and type I diabetes. The methods can be used to treat or prevent such disorders in patients having or at risk of such disorders. Patients having a disorder include those who are currently experiencing clinical symptoms, and patients who experience symptoms intermittently who may be symptomatic or asymptomatic at any particular time. These methods are particularly effective for treating a subject afflicted with multiple sclerosis comprising administering to the subject a therapeutically effective amount of an expressible nucleic acid encoding osteopontin. Also provided is a method of inhibiting the onset of multiple sclerosis in a subject comprising administering to the subject a prophylactically effective amount of an expressible nucleic acid encoding osteopontin.

1. Nucleic Acids Encoding Osteopontin

The nucleic acids used in these methods encodes osteopontin or an epitopic fragment thereof. The nucleic acids are transcribed and translated (DNA) or transcribed (mRNA) in situ, and the translation product generates an immune response. DNA immunization is described by WO 99/28471, Chowdhury et al., *PNAS* 95, 669-674 (1998) and *J. Immunol. Methods* 231, 83-91 (1999)).

DNA immunization can be performed with or without an adjuvant. The adjuvant, if present, can be one that is typically used with a protein antigen (see below), or it can be an adjuvant that is specifically chosen to associate with DNA, such as the positively charged detergent CTAB. The DNA can be administered naked or complexed with colloidal materials. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient lipofection of polynucleotides include those of Felgner, WO 91/17424, WO 91/16024.

Optionally, the DNA is dissolved in a pharmaceutical carrier in a solution that is sterile and substantially isotonic.

The nucleic acid used as an immunogen contains a segment encoding osteopontin and other segments encoding one or more regulatory sequences that ensure translation and transcription (in the case of DNA) of the immunogen. Regulatory sequences include a promoter, enhancer, transcription termination site, ribosome binding site, and intronic sites. The promoter can be constitutive or inducible or tissue specific, in which case the promoter is preferably specific for antigen presenting cells. For expression in blood cells, as is desirable for induction of an immune response, promoter and enhancer elements from light or heavy chain immunoglobulin genes or the CMV major intermediate early promoter and enhancer are suitable to direct expression. Optionally, DNA immunogens is present as a component of a vector. In some instances, the vector encodes proinflammatory cytokines to attract immune cells to the site of injection. In some instances, the DNA encodes a fusion protein, comprising an antigenic component to which antibodies are desired and a T-cell antigen, such as tetanus toxoid, or other adjuvant such as C3d (see Dempsey et al., Science 271, 348-50 (1996)). The DNA can encode a full length protein or a desired epitopic fragment thereof.

In a further variation, the nucleic acid can be incorporated into the genome of a virus or a bacteria. Optionally, the nucleic acid is incorporated in such a manner that the immunogenic peptide is expressed as a secreted protein or as a fusion protein with an outer surface protein of a virus or a transmembrane protein of a bacteria so that the peptide is displayed. Viruses or bacteria used in such methods should be nonpathogenic or attenuated. Suitable viruses include adenovirus, HSV, Venezuelan equine encephalitis virus and other alpha viruses, vesicular stomatitis virus, and other rhabdo viruses, vaccinia and fowl pox. Suitable bacteria include Salmonella and Shigella. Fusion of an immunogenic peptide to HBsAg of HBV is particularly suitable.

2. Administration of Osteopontin

The invention also provides methods in which osteopontin or an epitopic fragment thereof is administered to a patient. The osteopontin generates an immune response which lowers levels of osteopontin in the patient in the same manner as described for nucleic acids encoding osteopontin administration. Osteopontin can be administered alone or fused as a component of a longer protein. Optionally such a fusion protein can include a heterologous amino acid sequence that induces a helper T-cell response against the heterologous amino acid sequence and thereby a B-cell response against osteopontin.

Epitopic fragments of osteopontin suitable for use in the methods can be initially screened by standard computer programs that identify regions of probable immunogenicity. Fragments are then tested for activity in animal models as described in the Examples.

3. Adjuvants

A variety of adjuvants can be used in combination with osteopontin or epitopic fragments thereof or nucleic acids encoding the same to elicit an immune response. Preferred adjuvants include aluminum hydroxide and aluminum phosphate, 3 De-O-acylated monophosphoryl lipid A (MPL™) (see GB 2220211 (RIBI ImmunoChem Research Inc., Hamilton, Mont., now part of Corixa). Stimulon™ QS-21 is a triterpene glycoside or saponin isolated from the bark of the Quillaja Saponaria Molina tree found in South America (see Kensil et al., in Vaccine Design: The Subunit and Adjuvant Approach (eds. Powell & Newman, Plenum Press, NY, 1995); U.S. Pat. No. 5,057,540),(Aquila BioPharmaceuticals, Framingham, Mass.). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (WO 98/40100).

4. Therapeutic and Prophylactic Regimes for Generating an Immune Response

In prophylactic applications, pharmaceutical compositions or medicants are administered to a patient susceptible to, or otherwise at risk of, an osteoponin related disorder in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicants are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. An effective regime comprises a combination of an effective dosage and frequency of administration. Typically, the immune response is monitored and repeated dosages are given if the immune response starts to wane.

Effective doses of the compositions of the present invention vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. The amount of immunogen depends on whether adjuvant is also administered, with higher dosages being required in the absence of adjuvant. The amount of immunogen depends on whether adjuvant is also administered, with higher dosages being required in the absence of adjuvant. The amount of an immunogen for administration sometimes varies from 1-500 µg per patient and more usually from 5-500 µg per injection for human administration. Occasionally, a higher dose of 1-2 mg per injection is used. Typically about 10, 20, 50 or 100 µg is used for each human injection. The timing of injections can vary significantly from once a day, to once a year, to once a decade. A typical regimen consists of an immunization followed by booster injections at time intervals, such as 6 week intervals. Another regimen consists of an immunization followed by booster injections 1, 2 and 12 months later. Another regimen entails an injection every two months for life. Alternatively, booster injections can be on an irregular basis as indicated by monitoring of immune response.

Doses for nucleic acids encoding immunogens range from about 10 ng to 1 g, 100 ng to 100 mg, 1 µg to 10 mg, or 30-300 µg DNA per patient.

In order to facilitate an understanding of the Experimental Details section that follows, certain frequently occurring methods and/or terms are best described in Sambrook, et al. (40).

This invention will be better understood by reference to the Examples which follow, but those skilled in the art will readily appreciate that the information detailed is only illustrative of the invention as described more fully in the claims which follow thereafter.

EXAMPLES

Synopsis

Multiple sclerosis is a demyelinating disease, characterized by inflammation in the brain and spinal cord, possibly due to autoimmunity. Large scale sequencing of cDNA libraries, derived from plaques dissected from brains of patients with MS, indicated an abundance of transcripts for osteopontin. Microarray analysis of spinal cords from rats paralyzed from experimental autoimmune encephalomyelitis ("EAE"), a model of MS, also revealed increased OPN transcripts. Osteopontin-deficient mice were resistant to progressive EAE and had frequent remissions, and myelin-reactive T cells in OPN−/− mice produced more IL-10 and less γ-interferon than in OPN+/+ mice. Osteopontin thus appears to regulate Th1-mediated demyelinating disease, and offers a target in blocking development of progressive MS, as well as other osteopontin-mediated diseases.

Discussion

We investigated a role for OPN in MS and in an experimental model for MS, experimental autoimmune encephalomyelitis ("EAE") in mice. Initially we set out to identify gene transcripts involved in the inflammatory response that might be increased in the central nervous system ("CNS") during active EAE, and that returned to nomial when EAE was successfully treated after the onset of paralysis. Customized oligonucleotide microarrays were produced to monitor transcription of genes involved in inflammatory responses (12 and 13). Details concerning these custom microarrays are set forth in the Methods section below.

These initial microarray experiments showed that osteopontin transcripts were elevated in the brains of rats with EAE, and not in brains of rats protected from EAE. Details of these experiments and others relevant to the subject invention are set forth in the Methods section below.

In parallel, we performed high throughput sequencing of expressed sequence tags [EST], utilizing non-normalized cDNA brain libraries (15, 16, 17), generated from MS brain lesions and control brain. Using this protocol the mRNA populations present in the brain specimens are accurately represented, enabling the quantitative estimation of transcripts and comparisons between specimens (Table 2 and Table 3). Molecular mining of two sequenced libraries and their comparison with a normal brain library, matched for size and tissue type, and constructed with an identical protocol, revealed that OPN transcripts were frequently detected, and were exclusive to the MS mRNA population, but not found in control brain mRNA (Table 2).

TABLE 2

MS-Specific Gene Transcripts

| Accession # | Geno description | MS1 abundance | MS2 abundance | Average clone count | Cellular function | Genomic location |
|---|---|---|---|---|---|---|
| S45630 | Alpha B-crystallin | 7 | 12 | 9.5 | cell structure/motility | 11q22.3-q23.1 |
| M61901 | Prostaglandin D synthase | 8 | 7 | 7.5 | cell signaling/cell communication | 9q34.2-34.3 |
| X75252 | Prostatic binding protein | 6 | 7 | 6.5 | cell signaling/cell communication | 12q24.1* |
| X53777 | Ribosomal protein L17 | 10 | 2 | 6 | gene/protein expression | 18q |
| X13694 | Osteopontin | 8 | 3 | 5.5 | cell structure/motility/signaling | 4q21-q25 |
| AB037797 | KIAA1376 | 6 | 3 | 4.5 | unclassified | 5 |
| Z19554 | Vimentin | 4 | 5 | 4.5 | cell structure/motility | 10p13 |
| X52947 | Cardiac gap junction protein | 5 | 3 | 4 | cell signaling/cell communication | 6q21-q23.2* |
| D17554 | DNA-binding protein | 4 | 4 | 4 | gene/protein expression | 12q23-24.1* |
| AF181862 | G protein-coupled receptor | 2 | 6 | 4 | cell signaling/cell communication | 16p12 |
| AB018321 | ATPase Na/K transporting, alpha 2 (KIAA0778) | 2 | 6 | 4 | cell signaling/cell communication | 1q21-q23 |
| AF100620 | MORF-related gene X | 1 | 7 | 4 | gene/protein expression | Xq22* |
| AB002363 | KIAA0365 | 1 | 7 | 4 | unclassified | 19p12 |
| AF072902 | Gp130 associated protein GAM | 6 | 1 | 3.5 | unclassified | 19p13.3 |
| M11233 | Cathepsin D | 6 | 1 | 3.5 | cell/organism defense | 11p15.5 |
| D78014 | Dihydropyrimidinase related protein-3 | 6 | 1 | 3.5 | metabolism | 5q32 |
| X53305 | Stathmin | 4 | 3 | 3.5 | cell division | 1p36.1-p35* |
| AF026844 | Ribosomal protein L41 | 4 | 3 | 3.5 | unclassified | 22q12 |
| U48437 | Human amyloid precursor-like protein 1 | 4 | 3 | 3.5 | unclassified | N/A |
| U51678 | Small acidic protein | 3 | 4 | 3.5 | unclassified | N/A |
| U67171 | Selenoprotein W | 3 | 4 | 3.5 | metabolism | 19q13.3* |
| S80794 | Tyrosine and tryptophan hydroxylase activator | 2 | 5 | 3.5 | cell signaling/cell communication | 22q12.3 |
| AB011089 | KIAA0517 (brain) | 4 | 2 | 3 | unclassified | 4q28 |
| AAD32952 | PHR1 isoform 4 [Mus musculus] | 3 | 3 | 3 | unclassified | N/A |
| J04173 | Phosphoglycerate mutase, brain | 2 | 4 | 3 | metabolism | 10q25.3 |
| M22382 | Heat shock 60 kD protein 1 (chaperonin) | 2 | 4 | 3 | cell/organism defense | 2 |
| M34671 | HUMCD59A Human lymphocytic antigen CD59/MEM43 | 2 | 4 | 3 | unclassified | 11p13 |
| M64786 | Similar to Myc | 2 | 4 | 3 | unclassified | N/A |
| AJ132695 | Rac1 gene | 2 | 4 | 3 | cell signaling/cell communication | Xq26.2-27.2 |
| Z99716 | Septin 3 | 1 | 5 | 3 | cell division | 22q13.1 |
| U49436 | Human translation initiation factor 5 | 1 | 5 | 3 | gene/protein expression | 14q32* |
| CAA63354 | Cysteine string protein [Bos taurus] | 2 | 3 | 2.5 | unclassified | N/A |
| U90915 | Cytochrome c oxidase subunit IV | 4 | 1 | 2.5 | metabolism | 16q24.1 |
| J02611 | Apolipoprotein D | 4 | 1 | 2.5 | metabolism | 3q26.2-qter |
| X05607 | Cystatin C (cysteine proteinase inhibitor precursor) | 4 | 1 | 2.5 | metabolism | 20p11.2 |
| U45976 | Clathrin assembly protein lymphoid myeloid leukemia | 4 | 1 | 2.5 | unclassified | 11q14 |
| J00272 | Metallothionein-II pseudogene | 4 | 1 | 2.5 | unclassified | 4p11-q21 |
| S69965 | Beta-synuclein | 3 | 2 | 2.5 | unclassified | 5q35 |

TABLE 2-continued

MS-Specific Gene Transcripts

| Accession # | Geno description | MS1 abundance | MS2 abundance | Average clone count | Cellular function | Genomic location |
|---|---|---|---|---|---|---|
| Y00711 | Lactate dehydrogenase B | 3 | 2 | 2.5 | metabolism | 12p12.2-p12.1 |
| L37033 | FK-506 binding protein homologue (FKBP38) | 3 | 2 | 2.5 | cell signaling/cell communication | 19p12 |
| AF044956 | NADH: ubiquinone oxidoreductase B22 subunit | 3 | 2 | 2.5 | metabolism | 8q13.3 |
| AB011154 | KIAA0582 (brain) | 3 | 2 | 2.5 | unclassified | 2p12 |
| X55039 | Centromere autoantigen B | 3 | 2 | 2.5 | unclassified | 20p13 |
| X64364 | Basigin | 3 | 2 | 2.5 | cell signaling/cell communication | 19p13.3 |
| U82761 | S-adenosyl homocysteine hydrolase-like 1 | 3 | 2 | 2.5 | metabolism | 1 |
| D13627 | Chaperonin containing TCP1, subunit B (theta) | 2 | 3 | 2.5 | gene/protein expression | 21q22.11 |
| Z47087 | Transcription elongation factor B (SIII), polypeptide like | 2 | 3 | 2.5 | gene/protein expression | 5q31 |
| X75861 | Testis enhaced gene transcript | 2 | 3 | 2.5 | cell division | 12q12-q13 |
| M16447 | Quinoid dihydropteridine reductase | 2 | 3 | 2.5 | metabolism | 4p15.31 |
| M22918 | Non-muscle myosin alkali light chain | 2 | 3 | 2.5 | unclassified | 12 |
| M55270 | Matrix Gla protein | 2 | 3 | 2.5 | unclassified | 12p13.1-p12.3 |
| AF151807 | CGI-49 protein | 2 | 3 | 2.5 | unclassified | 1 |
| AAD45960 | Human EST H08032.1 (NID: g872854) | 2 | 3 | 2.5 | unclassified | 7q11.23-q21.1 |

Only genes with a mean fold change of >2.5 are listed.
"N/A" indicates that mapping position is not known.
*indicates genomic regions that reached nominal criteria of linkage in genome-wide screenings.

We sequenced more than 11,000 clones from MS libraries 1 and 2, and control libraries (FIGS. 1A-1C), and focused our analysis on genes present in both MS libraries, but absent in the control library. This yielded 423 genes, including 26 novel genes. From those, 54 genes showed a mean fold change of 2.5 or higher in MS libraries 1 and 2 (Table 2). Transcripts for alpha B-crystallin, an inducible heat shock protein, localized in the myelin sheath, and known to be targeted by T cells in MS, were the most abundant transcripts unique to MS plaques (19) (Table 2). The next five most abundant transcripts, included those for prostaglandin D synthase, prostatic binding protein, ribosomal protein L17, and OPN.

Next, we analyzed all genes present in each of the three cDNA libraries, and found 330 (seven novel) genes. Based on the clone count of each sequenced gene, a table was constructed with transcripts showing an average fold difference equal to or greater than ±2.00 between MS and control.

Forty of these transcripts were divided into three levels, on the basis of the consistency of differential expression across libraries (Table 3). Some of these genes (Table 3) were myelin basic protein (MBP), heat shock protein 70 (HSP-70), glial fibrillary acidic protein (GFAP) and synaptobrevin. MBP transcripts displayed consistent high levels of expression in the three libraries, indicating a very high turnover rate for this protein. Expression of HSP70-1, which is involved in myelin folding (20), was significantly elevated. Although not differentially expressed, GFAP was among the three most abundant species in all the libraries, consistent with a prominent glial (or astrocytic) response in the MS brains. Six genes belonging to the KIAA group of large-size cloned mRNAs showed differential expression. The decreased transcription of synaptobrevin is important given that it belongs to a family of small integral membrane proteins specific for synaptic vesicles in neurons. Recent evidence indicates that axonal loss is one of the major components of pathology in MS (21, 22).

TABLE 3

Genes Differentially Expressed in MS and Normal Libraries

| Accession # | Gene description | Clone count MS1 | MS2 | CTRL | Average Fold-difference | Cellular function | Genomic location |
|---|---|---|---|---|---|---|---|
| M17885 | Acidic ribosomal phosphoprotein P0 | 9 | 13 | 2 | 5.2 | gene/protein expression | 12q24* |
| X16869 | Elongation factor 1-alpha | 32 | 33 | 15 | 2.07 | gene/protein expression | 6q14 |
| M54927 | Myelin proteolipid protein | 41 | 16 | 64 | −3 | cell structure/motility | Xq22* |
| U66623 | Small GTPase | 1 | 1 | 7 | −7.35 | cell signaling/cell communication | 2q21.2 |
| M26252 | Piruvate kinase, muscle | 2 | 1 | 10 | −8.04 | Energy metabolism | 15q22 |
| M59828 | Heat shock protein 70-1 | 2 | 14 | 1 | 7.29 | cell/organism defense | 6q21.3* |
| AF068848 | Scaffold attachement factor A | 6 | 1 | 1 | 2.49 | Cell division | N/A |
| AF035283 | Clone 23916 | 10 | 15 | 5 | 2.36 | unclassified | N/A |
| U46571 | Tetratricopeptide repeat protein 2 | 10 | 4 | 3 | 2.29 | unclassified | 17q11.2 |
| AF131756 | clone 24912 | 2 | 10 | 10 | −3.02 | unclassified | N/A |
| X92845 | N-myc downstream regulated | 1 | 7 | 7 | −4 | unclassified | 8q24.1 |
| M97168 | X (Inactive)-specific transcript | 1 | 13 | 10 | −4.33 | unclassified | Xq13.2 |
| AB023167 | Neural membrane protein 35 (KIAA0950) | 1 | 3 | 7 | −4.74 | unclassified | 12q13 |

TABLE 3-continued

Genes Differentially Expressed in MS and Normal Libraries

| | | Clone count | | | Average | | Genomic |
|---|---|---|---|---|---|---|---|
| Accession # | Gene description | MS1 | MS2 | CTRL | Fold-difference | Cellular function | location |
| AB002391 | HERC2 (KIAA0393) | 2 | 1 | 7 | −5.63 | unclassified | 15q13 |
| AF055026 | RaP2 interacting protein 3 | 1 | 1 | 6 | −6.3 | Unclassified | 17 |
| U89330 | Microtubule-associated protein 2 | 1 | 1 | 6 | −6.3 | cell structure/motility | 2q34-q35 |
| M20020 | Ribosomal protein S6 | 5 | 6 | 1 | 5.23 | gene/protein expression | 9p21* |
| X03747 | Na/K-ATPase beta subunit | 5 | 5 | 1 | 4.78 | Energy metabolism | 1q22-q25 |
| V00572 | Phosphoglycerate kinase | 5 | 4 | 1 | 4.33 | metabolism | Xq13 |
| M59488 | S100 protein beta-subunit | 5 | 4 | 1 | 4.33 | cell signaling/ cell communication | Z1q22.3 |
| AB018271 | KIAA0728 (Brain) | 4 | 4 | 1 | 3.83 | Unclassified | 6p11-11.2 |
| AB020718 | KIAA0911 | 4 | 3 | 1 | 3.38 | unclassified | 1p36* |
| AAD02202 | CsM-KII inhibitory protein [*Rattus norvegicus*] | 2 | 5 | 1 | 3.26 | unclassified | N/A |
| D67025 | Proteasome 26S subunit (non-ATPase, 3) | 1 | 1 | 3 | −3.15 | cell/organism defense | 17q21.1 |
| D63424 | Glycogen synthase kinase 3 alpha | 1 | 1 | 3 | −3.15 | metabolism | 19q13.3-13* |
| AF051976 | Unconventional myosin XV | 1 | 1 | 3 | −3.15 | cell structure/motility | 17p11.2 |
| X13916 | LDL-receptor related protein | 1 | 1 | 3 | −3.15 | metabolism | 12q13.q14 |
| AB028981 | KIAA1058 | 1 | 1 | 3 | −3.15 | unclassified | 13 |
| AF102846 | N-ethylmalelmide-sensitive factor | 3 | 1 | 5 | −3.61 | metabolism | 17q21 |
| L10284 | Calnexin | 3 | 1 | 5 | −3.61 | cell/organism defense | 5q35 |
| D88435 | Cyclin G associated kinase | 1 | 2 | 5 | −3.85 | cell division | 4p16 |
| AF054987 | aldolase C | 2 | 1 | 5 | −4.02 | metabolism | 17cen-q12 |
| CAB01750 | similar to Mitochondrial carrier proteins [*Caenorhabditis elegans*] | 1 | 1 | 4 | −4.2 | Unclassified | N/A |
| AL137406 | Clone DKFZp434M162 | 1 | 1 | 4 | −4.2 | Unclassified | N/A |
| AB032436 | Brain specific Na+-dependent inorganic phosphate cotransporter | 1 | 1 | 4 | −4.2 | metabolism | 19q13* |
| L10911 | Splicing factor(CC1.3) | 1 | 1 | 4 | −4.2 | gene/protein expression | 20 |
| L77864 | Amyloid beta (A4) precursor protein-binding, family B, member 1 (Fe65) | 1 | 4 | 7 | −4.42 | unclassified | 11p15 |
| U64520 | Synaptobfevin-3 | 1 | 1 | 5 | −5.25 | unclassified | 1p35-p36 |
| D87465 | KIAA0275 (brain) | 1 | 1 | 5 | −5.25 | unclassified | 10 |

Only genes corresponding to transcripts with an average fold difference of ≧2 are listed. The first section of the table lists genes whose expression was statistically significant in both MS libraries when compared to the CTRL library (Fisher's exact test, $p < 0.05$). The second section contains genes with significant difference in expression in only one of the MS libraries and the CTRL. The last section includes genes with non-significant differences but AFD ≧ ±3.00.
N/A, mapping position is not known.
*genomic regions that reached nominal criteria of linkage in genome-wide screenings.

Figures 2A, 2B, 2C, 2D, 2E, 2F, 2G, 2H:
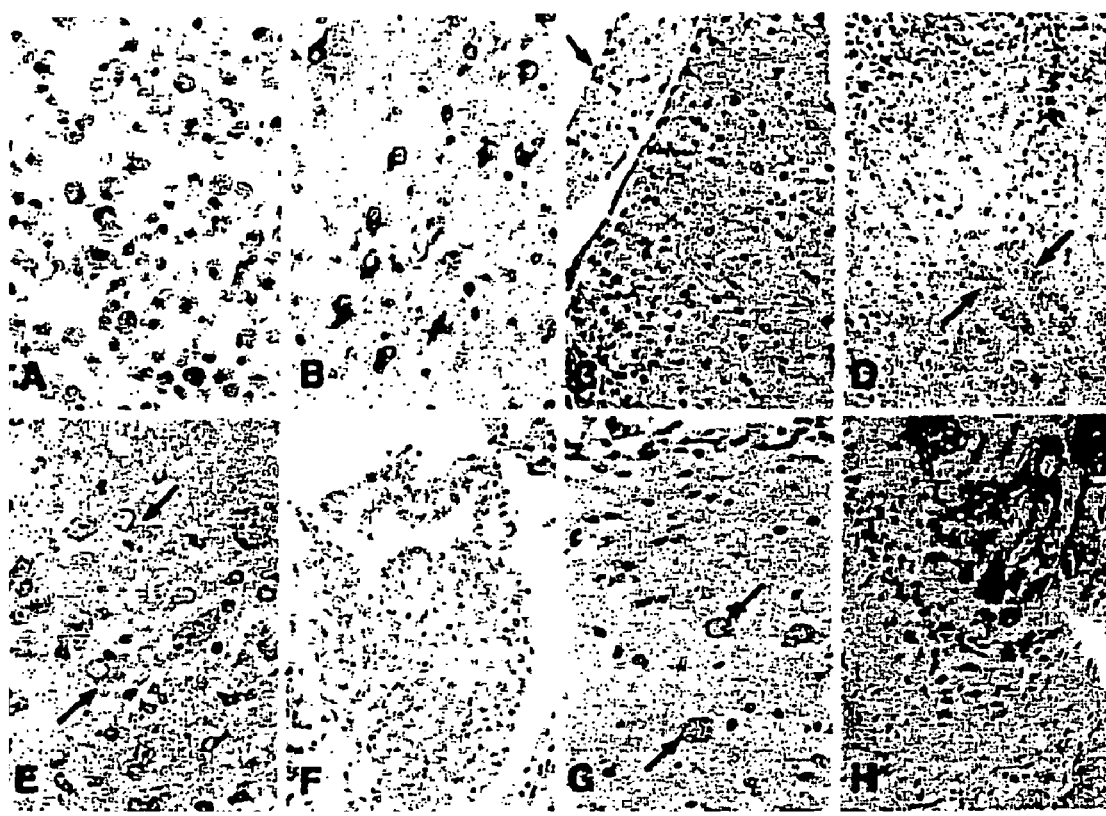
FIGS. 2A and 2B OPN in macrophages is shown in the center of an actively demyelinating MS plaque (1A) and in white matter astrocytes adjacent to an active MS plaque (1B). OPN staining was performed with a polyclonal anti-OPN antibody on paraffin-embedded sections. All photos in FIGS. 2A-2H are immunoperoxidase-stained with diaminobenzidine chromogen and hematoxylin counterstain. Magnifications: A-D, F, H=370×; E, G=494×.
FIGS. 2C-2F These Figures show relapsing-remitting EAE in mice. EAE was induced in nine SJL mice (The Jackson Laboratory, Bar Harbor, Me.) with PLP 139-151, as previously described (24). Four mice injected with PBS served as controls. Immunostaining was performed with the anti-OPN antibody MPIIIB10$_1$ (Developmental Studies Hybridoma bank, Iowa City, Iowa) (25) and slides were examined by a blinded observer.
FIG. 2G This Figure relates to acute EAE in rat. EAE was induced in 19 Lewis rats (The Jackson Laboratory) as described in (13) but with 400 μg GPSCH. Four rats injected with CFA alone served as controls. Brains were processed and stained with MPIIIB10$_1$. Microglial expression of OPN around inflammatory lesions (G) correlated with the clinical disease severity. OPN was also expressed in neurons (arrows), mostly in the animals with severe clinical signs.
FIG. 2H This Figure shows a positive control, i.e., OPN staining in the bony growth plate of a mouse femur with MPIIIB10$_1$.

Given the known inflammatory role for OPN, we examined the cellular expression pattern of this protein in human MS plaques and in control tissue, by immunohistochemistry. To identify cells expressing OPN in situ we used a polyclonal antibody, generated in mouse against recombinant glutathione S-transferase (GST)-OPN, to stain postmortem MS and control tissue samples (23) (FIGS. 2A and 2B). Within active MS plaques OPN was found on microvascular endothelial cells and macrophages (FIG. 2A), and in white matter adjacent to plaques. Reactive astrocytes and microglia also expressed OPN (FIG. 2B).

The role of OPN in inflammatory demyelinating disease was next examined using two models of EAE (1). A relapsing-remitting model of EAE was first used to compare the cellular expression of OPN at different stages of the disease. Disease was induced in SJL mice by immunization with the proteolipid protein peptide 139-151 (PLP139-151) in complete Freund's adjuvant (CFA), and the animals were scored daily for signs of disease (24). Brain and spinal cord were removed during acute phase, remission or first relapse. Histopathologic identification of OPN in EAE was then performed. (FIGS. 2C-2F). OPN was expressed broadly in microglia during both relapse and remission from disease, and this expression was focused near perivascular inflammatory lesions. In addition to OPN expression on glia, expression in neurons was detectable during acute disease, and relapse, but not during remission. To confirm the expression of OPN in an acute form of EAE, a rapid, monophasic demyelinating disease was induced in Lewis rats (12), then OPN immunostaining was performed on their brains (FIG. 2G). OPN expression in microglia and neurons was predominant in the sick rats, and was focused close to the acute lesions, as was observed in the relapsing-remitting mouse model of EAE. Staining of OPN in bone with the same antibody, MPIIIB10$_1$, served as a positive control (FIG. 2H). These results show the role of OPN in acute, as well as in relapsing forms of EAE, and indicate that the degree of expression of OPN in lesions correlated with the severity of disease.

Figures 3A, 3B:
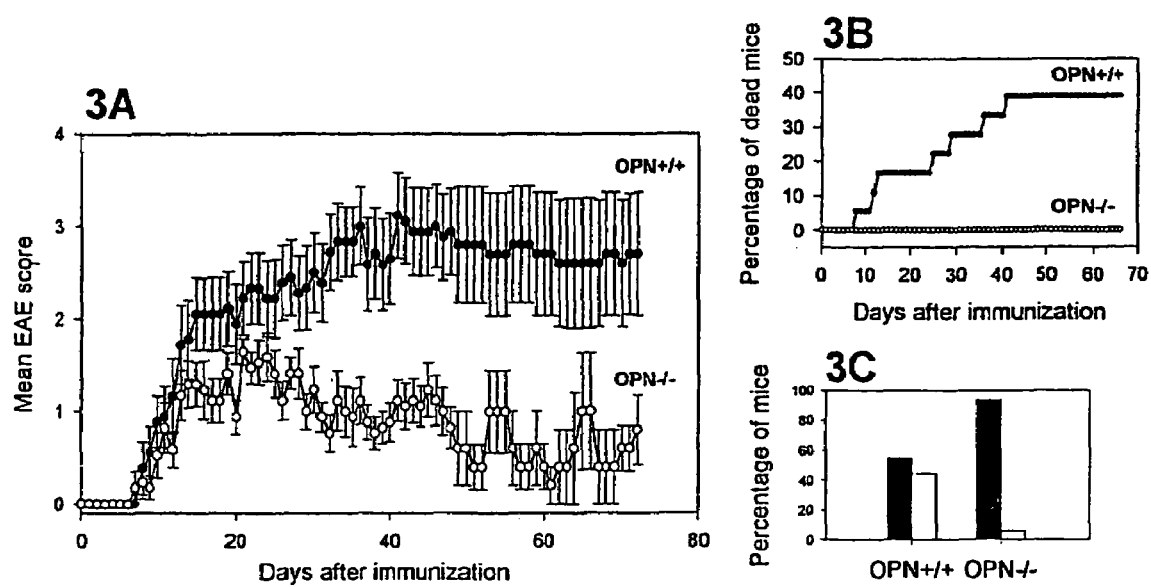

The role of OPN in demyelinating disease was next tested using OPN deficient mice (FIGS. 3A-3C) (30). EAE was induced using myelin oligodendrocyte glycoprotein peptide 35-55 (MOG 35-55) in CFA in OPN−/− mice and OPN+/+ controls (31). EAE was observed in 100% of both OPN+/+ and OPN−/− mice with MOG 35-55. Despite this, severity of disease was significantly reduced in all animals in the OPN−/− group (FIG. 3A), and these mice were totally protected from EAE-related death (FIG. 3B). Thus, OPN significantly influenced the course of progressive EAE induced by MOG 35-55.

The rate of relapses and remissions was next tested. During the first 26 days, OPN−/− mice displayed a distinct evolution of EAE, with a much higher percentage of mice having remissions compared with the controls (FIG. 3C). OPN+/+ and OPN−/− mice were killed on days 28, 48, and 72 after immunization for histopathology. Although the clinical courses in the two groups were quite different, there were similar numbers and appearances of inflammatory foci within the CNS.

To examine whether different immune responses were involved in OPN−/− and OPN+/+ animals, we tested the profile of cytokine expression in these mice. Because EAE is a T cell-mediated disease, we first analyzed the T cell proliferative response to the auto-antigen MOG 35-55 in the OPN−/− mice. T cells in OPN−/− mice showed a reduced proliferative response to MOG 35-55, compared with OPN+/+ T cells (FIG. 4A). In addition, IL-10 production was increased in T cells reactive to MOG 35-55 in OPN−/− mice that had developed EAE, compared with T cells in OPN+/+ mice (FIG. 4B). At the same time, IFN-γ and IL-12 production was diminished in the cultures of spleen cells stimulated with MOG (FIGS. 4C-4D).

Because IFN-γ and IL-12 are important pro-inflammatory cytokines in MS (1, 33), the finding that in OPN−/− mice there is reduced production of these cytokines, is consistent with the notion that OPN plays a critical role in the modulation of Th1 immune responses in MS and EAE. Further, IL-10 has been associated with remission from EAE (34). In this context, the enhancement of myelin-specific IL-10 production in OPN−/− mice, may account for the tendency of these mice to go into remission. Sustained expression of IL-10 may thus be an important factor in the reversal of relapsing MS, and its absence may allow the development of secondary progressive MS.

In conclusion our data show that OPN may has pleiotropic functions in the pathogenesis of demyelinating disease. OPN production by glial cells may lead to the attraction of Th1 cells, and its presence in glial and ependymal cells may allow inflammatory T cells to penetrate the brain. Finally, our data suggest that neurons may also secrete this proinflammatory molecule and participate in the autoimmune process. Potentially, neuronal OPN secretion could modulate inflammation and demyelination, and could influence the clinical severity of the disease. Consistent with this idea, a role for neurons in the pathophysiology of MS and EAE has recently been described (21,22), and neurons are known to be capable of cytokine production (35, 36). OPN inhibits cell lysis (6), and thus neuronal OPN might even protect the axon from degeneration during autoimmune demyelination.

CD44 is a known ligand of OPN, mediating a decrease of IL-10 production (10). As shown here, OPN−/− mice produced elevated IL-10 during the course of EAE. We recently demonstrated that anti-CD44 antibodies prevented EAE (37), suggesting that the proinflammatory effect of OPN in MS and EAE might be mediated by CD44. The binding of OPN to its integrin fibronectin receptor $a_v b_3$ through the arginine-glycine-aspartate tripeptide motif may also perpetuate Th1 inflammation (10). In active MS lesions, the $a_v$ subunit of this receptor is overexpressed in macrophages and endothelial cells, and the $b_3$ subunit is expressed on endothelial cell luminal surfaces (23). By means of its tripeptide-binding motif, OPN inhibits inducible nitric oxide synthetase (iNOs) (38), which is known to participate in autoimmune demyelination (1). Thus in conclusion, OPN is situated at a number of checkpoints that would allow diverse activities in the course of autoimmune-mediated demyelination.

Methods

Custom Microarrays

Custom microarrays were designed that allow large scale profiling of mRNA for 517 components of the inflammatory response, including cytokines, chemokines, various adhesion molecules, and matrix metalloproteases. Profiles of mRNA transcripts from the spinal cord of six Lewis rats with EAE were analyzed. Rats were immunized with 400 mg of guinea pig spinal cord homogenate [GPSCH] and monitored for EAE as previously described (12). mRNA was isolated from the brain and spinal cord of three rats with hind limb paralysis (mean EAE score 2.7, indicating severe paraplegia), 15 days after immunization with GPSCH, and from three rats treated with a metalloprotease inhibitor after the initiation of EAE. It is established that matrix metalloprotease inhibitors can reverse EAE (13), and rats treated with the metalloprotease inhibitor [RS110379] displayed no clinical disease (mean EAE score 0.2). Spinal cord from two other normal rats served as controls.

OPN transcripts were increased 3.4 fold in the spinal cord of rats with EAE and paralysis, compared to controls without EAE (average difference change for intensity of OPN transcripts was 16609 fluorescent units in untreated rats with EAE versus an average difference change for intensity in OPN transcripts of 4846 in rats without EAE). After treatment with RS110379, levels of OPN mRNA were no different than control rats without EAE. Thus, there was a 1.1 fold change between the intensity of OPN transcripts in EAE rats treated with MMP inhibitor versus rats without EAE (the average difference of the change in intensity of OPN transcripts on the custom microarrays was 5176 units in rats treated with RS110379 versus an average difference intensity of 4846 units in rats without EAE).

Non-Normalized cDNA Brain Libraries

In contrast to normalized libraries in which high frequency transcripts are preferentially eliminated by nuclease treatment of DNA/RNA hybrids to facilitate detection of rare RNA species, we produced non-normalized libraries, where manipulation of clones is avoided. White matter brain tissue from the plaques of 3 MS patients was collected and frozen within two hours after death. Patient history on the specimen used for the first library (herein MS1) included clinically definite MS, and the presence of active inflammatory lesions. Material for the second MS library (herein MS2) came from a pool of tissues from two patients, one with acute, active lesions and widespread inflammatory involvement in the white matter, and the other with chronic, "silent" lesions, with gliosis, but without evidence of a lymphocytic infiltrate. The control library (CTRL) was constructed using pooled mRNA isolated from midbrain white matter, inferior temporal cortex, medulla, and posterior parietal cortex tissue removed from a 35-year-old Caucasian male who died from cardiac failure and who had no neuropathological changes. The libraries were made in collaboration with Incyte Genomics. Libraries were constructed using 1.5 mg of polyA RNA from each sample. cDNA synthesis was initiated using a NotI-anchored oligo(dT) primer. Double-stranded cDNA was blunted, ligated to EcoRI adaptors, digested with NotI, size-selected, and cloned into the NotI and EcoRI sites of the pTNCY vector (Incyte, Palo Alto, Calif.). Approximately 4,000 clones from each library were sequenced in ABI automatic DNA Sequencer (Applied Biosciences, Foster City, Calif.). Annotated data was extracted from the Incyte database LifeSeq Gold® and incorporated into MS Access 2000® and MS Excel 2000® for further analysis. All queries were designed and performed in MS Access, while charts and tables were generated with MS Excel. Cellular roles were assigned after consulting the Expressed Gene Anatomy Database (EGAD, The Institute for Genomic Research, www.tigr.org/egad). Genomic location was included according to NCBI's Map-View and Genemap'98 (National Institute for Biotechnology Information, www.ncbi.nlm.nih.gov). Comparisons of gene frequencies between each MS library and the CTRL were performed and the average fold change calculated. Differences in gene expression were subjected to Fisher's exact test and a P-value of 0.05 or lower, was selected as criteria for inclusion in each comparison. Results of these experiments are shown in FIGS. 1A-1C.

We sequenced 3678, 4174, and 3740 clones from MS1, MS2, and control libraries, respectively. Each of the libraries had a substantial number of clones with no match to the Genbank database, and were thus considered novel. Clones in library MS1 could be assigned to 2387 different cDNA species from which 331 corresponded to novel genes. MS2 and CTRL yielded 2727 (546 novel) and 2352 (511 novel) species respectively. Analysis of frequency distribution revealed a similar pattern for all three libraries, with the most abundant transcripts being represented by few species including two myelin genes, myelin basic protein, [MBP], and proteolipid protein, [PLP], and the astrocyte-specific transcript, glial fibrillary acidic protein, [GFAP]. Similarly, there was an exponentially decreasing frequency observed for less frequent cDNA species in all three libraries. Taken together the data reveal that the composition and complexity of the three libraries were similar, and that there were no obvious biases, therefore enabling comparative analysis.

Immunostaining

Mice were killed during relapse and remission and perfused with 60 ml of 10% formalin. Brain and spinal cord were removed and fixed in the same solution. Paraffin sections (6-10 µm) were prepared. OPN was detected with the monoclonal anti-OPN antibody MPIIIB10$_1$ (Developmental Studies Hybridoma Bank, Iowa City, Iowa), at 1/50 dilution, using the vector Mouse On Mouse (M.O.M.) immunodetection kit (Vector Laboratories, catalogue no. PK 2200), the Vectastain® Elite ABC kit (Vector Laboratories, catalogue no. PK 6100) according to the manufacturer's instructions, and the substrate 3,3'-diaminobenzidine (0.5 mg/ml for 4 minutes). The intensity of the cellular staining was evaluated by an observer blinded to the experimental design according to a semiquantitative scale (three grades). MPIIIB10$_1$ stains OPN in immuniohistochemical sections from mice, though it does not recognize OPN on Western blots (26). The successful use of MPIIIB10$_1$ in mouse sections has been reported (27, 28).

Induction of EAE

We induced EAE with MOG 35-55 in CFA in 129/C57B1/6 OPN-/- mice, and 129/C57B1/6 OPN+/+ controls. Here we slightly modified the protocol: we injected 100 mg of MOG 35-55 emulsion subcutaneously in the flanks of each female at day 0, and 400 ng of Pertussis Toxin at day 0 and day 2. Seven OPN+/+ and 6 OPN-/- mice were examined on days 28, 48 and 72 post immunization for histopathology. Data are unpublished showing similar numbers and appearances of inflammatory foci within the central nervous system in the two groups.

Transcriptional Profiling with Custom Microarrays

Spinal cord was homogenized in TRIzol reagent (Gibco BRL) using a Polytron (Kinematica AG, Switzerland) and total RNA prepared according to the recommended protocol. mRNA was purified by two rounds of selection using oligo(dT) resin (Oligotex, Qiagen). 2 mg of mRNA was used to prepare double stranded cDNA (Superscript, Gibco BRL). The primer for cDNA synthesis contained a T7 RNA polymerase promoter site. 1 mg of cDNA was used for an in-vitro transcription reaction (Ambion T7 Megascript) with biotinylated CTP and UTP (Enzo Diagnostics, Inc.). The labeling procedure amplifies the mRNA population ~60-fold. Microarray chips (GeneChip™ System, Affymetrix) were hybridized for 16 hours in a 45° C. incubator with constant rotation at 60 rpm. Chips were washed and stained on a fluidics station, and scanned using a laser confocal microscope. Affymetrix provided the procedures for sample preparation, fluidics station, scanner, and computer workstation. Chips were analysed with GeneChip v3.1 software, and scaled to a value of 150. The software determines whether a particular RNA transcript is present or absent, based on the intensity of the signal. Fold change was calculated by divided the intensity of the average difference change in the experimental sample by the intensity of the average difference change in the control.

Example 2

A Method to Treat Multiple Sclerosis and Other Autoimmune Diseases with DNA Encoding Osteonontin Treatment of mice with DNA encoding murine (i.e., "self protein") osteopontin induces an anti-osteopontin immunoglobulin response in the host that inhibits the detrimental impact of osteopontin in perpetuating the disease.

DNA encoding murine osteopontin was generated by cloning DNA encoding osteopontin into the pCDNA3 mammalian expression vector. pCDNA3 contains the CMV promoter and SV-40 large T antigen poly adenylation signal. This osteopontin-encoding vector was produced in *E. coli* and endotoxin-free DNA was purified using the Qiagen Endo-free Mega-prep kits (Qiagen, Valencia, Calif.).

Figure 5:
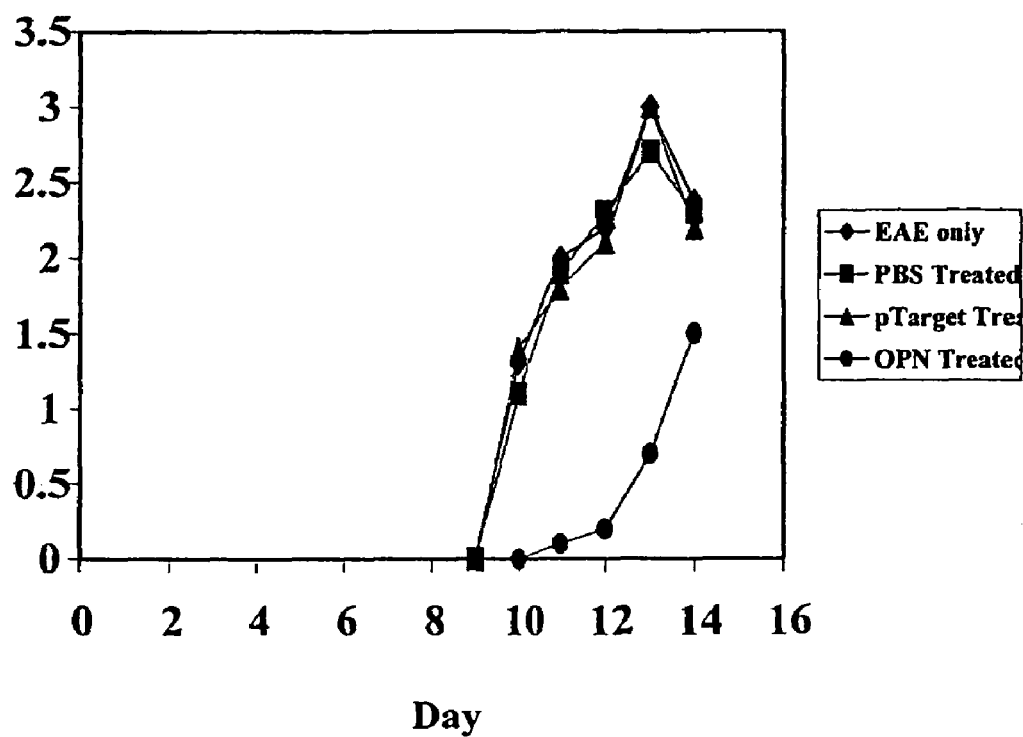
FIG. 5 This Figure shows that treatment with DNA encoding osteopontin reduces the incidence and severity of EAE. C57B6 mice were treated with DNA encoding osteopontin.

Mice are injected in the quadricep with 0.1 ml of 0.25% bupivicaine-HCL (Sigma, St. Louis, Mo.) in PBS (0.05 ml per quadricep). Two days following, mice are injected with 0.05 ml of each "self-plasmid" DNA at 1.0 mg/ml in phosphate buffered saline with 0.9 mM calcium in each quadricep. The plasmid DNA is injected two more times at 2 to 4 week intervals. The efficacy of osteopontin-encoding self-vector induction of anti-osteopontin antibodies can be enhanced by co-delivery of CpG immunostimmulatory oligonucleotides and/or treatment with DNA encoding osteopontin fused to one or more C3d components. Enzyme-linked immunosorbent assays were used to monitor levels of anti-osteopontin antibodies, with induction of anti-osteopontin antibodies representing efficacy of the therapy. Mice were subsequently challenged to develop EAE with a myelin peptide (typically PLPp139-151) in complete Freund's adjuvant, and mice pre-treated with self-vector encoding osteoponin have a reduced incidence and severity of EAE as demonstrated in FIG. 5.

Alternatively, strains of mice susceptible to chronic relapsing EAE (for example, SJL mice) can be induced to develop EAE (for example, with PLPp139-151 in complete Freund's adjuvant) and osteopontin-self-vector therapy initiated at bi-weekly intervals in mice with established EAE to induce antibodies against osteopontin to treat the disease. Efficacy is measured based on a reduction in the overall disease severity and number of new episodes of clinical paralysis using standard scoring systems.

In humans with multiple sclerosis, osteopontin-self-vector therapy is initiated following diagnosis. Efficacy is monitored based on induction of anti-osteopontin antibodies in the patient with multiple sclerosis, as measured by ELISA analysis. Efficacy is further demonstrated based on the reduction in the number and size of brain lesions (as measured by MRI scanning), the reduction of the number of disease relapses (episodes of clinical paralysis), and the slowing of progression to disability.

Example 3

Mice were injected with 10 micromolar of cardiotoxin (Sigma) in the tibialis anterior muscle. Five days later mice were given 100 micrograms of plasmid with full length OPN in phosphate buffered saline with 0.9 mM calcium in the tibialis anterior muscle. The plasmid with OPN was injected three more times in intervals of 6-7 days. EAE was induced 7 days after the last injection, with myelin oligodendroglial glycoprotein 35-55. Controls were performed using no treatment, treatment with PBS or treatment with the plasmid without the insert. Treatment was assessed on a standard clinical scale relating to disability of the mice. Antibody titer was also measured in the mice as follows. ELISA plates were coated with 50 ng/well of mouse recombinant OPN (R&D Systems Catalog Number: 441-OP) at 4 degrees overnight. Plates were washed the second day with PBS and 0.1% Tween (ie PBST Buffer) 3-4 times and then blocked with PBS and 0.25% gelatin for 3 h at 37 degrees. Plates were then washed 5 times with PBST and then sera were added in serial dilutions for over night incubation at 4 degrees (the serum are diluted with PBST 0.25% gelatin). The next day plates were washed with PBST 6 times and goat anti-mouse osteopontin antibody was added (R&D Systems Catalog Number: AF808) at concentration of 1 ug/ml diluted in PBST 0.25% gelatin and incubate 1 h at 37 degrees Celsius. The plates were then incubated with anti goat Ab conjugated to alkaline phosphatase at a dilution of 1:30000 for 1 h. The plates were wash 6 times and the substrate p-NPP p-nitrophenylphosphate in PBS was added. After development of color, the plates were read at 405 nm wavelength.

Figure 6:
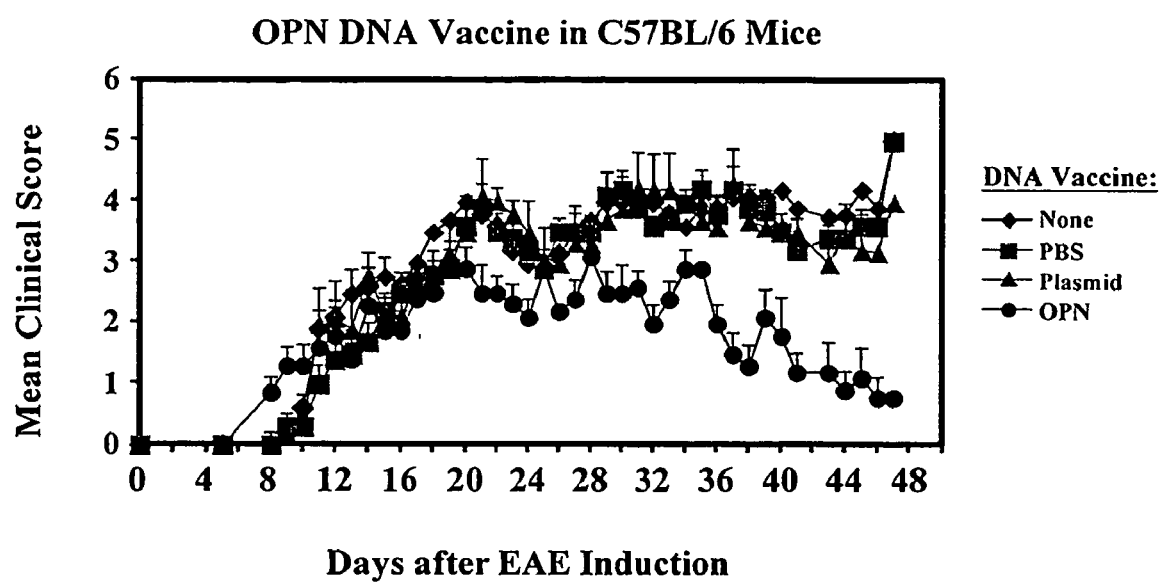
FIG. 6 This Figure shows that treatment with DNA encoding osteopontin reduces the incidence and severity of EAE. C57B6 mice were treated with DNA encoding osteopontin.
Figure 7:
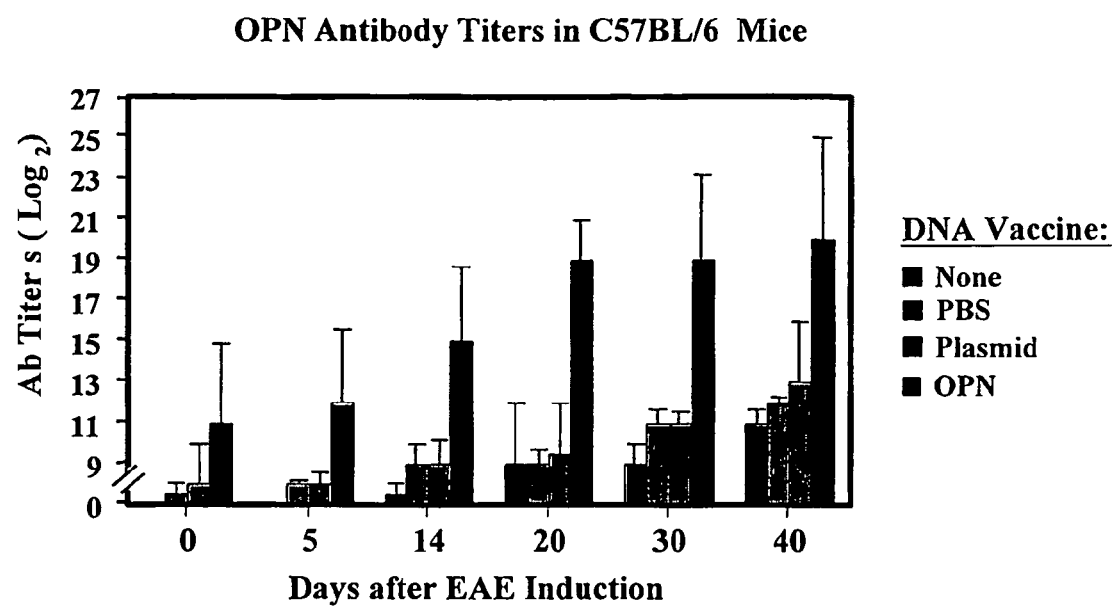
FIG. 7 This Figures shows antibody titers in the mice shown in FIG. 6.

FIG. 6 shows the results that treatment with the plasmid encoding OPN diminished clinical symptoms of EAE from day 24 to day 48, p<0.03, during the chronic phase of EAE. FIG. 7 shows that immunization with DNA encoding osteopontin generated an antibody titer that plateaued after about 20 days.

REFERENCES

1. L. Steinman, *Nature Immunology* 2, 762 (2001).
2. J. L. Haines et al., *Nat Genet* 13, 469 (1996).
3. G. C. Ebers et al., *Nat Genet* 13, 472 (1996).
4. S. Sawcer et al., *Nat Genet* 13, 464 (1996).
5. A. Oldberg, et al., *Proc Natl Acad Sci USA* 83, 8819 (1986).
6. L. W. Fisher, et al., *Biochem Biophys Res Commun* 280, 460 (2001).
7. D. T. Denhardt, X. Guo, *Faseb J* 7, 1475 (1993).
8. A. W. O'Regan et al., *Immunol Today* 21, 475 (2000).
9. S. R. Rittling, D. T. Denhardt, *Exp Nephrol* 7, 103 (1999).
10. S. Ashkar et al., *Science* 287, 860 (2000).
11. Steinman et al., *Mol. Med. Today* 1:79-83 (1995).
12. N. Karin et al., *J Immunol* 160, 5188 (1998).
13. K. Gijbels, R. E. Galardy, L. Steinman, *J Clin Invest* 94, 2177 (1994).
14. Steinman, *Nature* 375:739-740 (1995).
15. K. G. Becker et al., *J Neuroimmunol* 77, 27 (1997).
16. S. S. Choi et al., *Mamm Genome* 6, 653 (1995).
17. N. Sasaki et al., *Genomics* 49, 167 (1998).
18. Warren et al., *P.N.A.S.* 92:11061-11065) (1995).
19. J. M. van Noort et al., *Nature* 375, 798 (1995).
20. D. A. Aquino et al., *Neurochem Res* 23, 413 (1998).
21. D. Pitt, P. Werner, C. S. Raine, *Nat Med* 6, 67 (2000).
22. B. D. Trapp et al., *N Engl J Med* 338, 278 (1998).
23. R. A. Sobel et al., *J Neuropathol Exp Neurol* 54, 202 (1995).
24. R. Pedotti et al., *Nat Immunol* 2, 216 (2001).
25. Young, M. F., et al., *Genomics* 7: 491-502 (1990).
26. S. R. Rittling, F. Feng, *Biochem Biophys Res Commun* 250, 287 (1998).
27. N. Dorheim et al., *J Cell Phys* 154, 317 (1993).
28. C. Grainger *Nature Med* 1, 1063 (1995).
29. O'Regan et al., *Immunol Today* 21:475 (2000).
30. S. R. Rittling, et al., *J Bone Miner Res* 13, 1101 (1998).
31. A. Slavin et al., *Autoimmunity* 28, 109 (1998).
32. Ashkar et al., *Science* 287:860 (2000).
33. L. Steinman, *Cell* 85, 299 (1996).
34. M. K. Kennedy et al., *J Immunol* 149, 2496 (1992).
35. H. Villarroya et al., *J Neurosci Res* 49, 592 (1997).
36. S. L. Shin et al., *Neurosci Lett* 273, 73 (1999).
37. S. Brocke et al., *Proc Natl Acad Sci USA* 96, 6896 (1999).
38. S. M. Hwang et al., *J Biol Chem* 269, 711 (1994).
39. P. J. Ruiz et al., *J Immunol* 162, 3336 (1999).
40. Sambrook, et al., Molecular Cloning: A Laboratory Manual. 2nd Ed., New York: Cold Spring Harbour Laboratory Press (1989).

All publications and patent filings cited in this application are incorporated by reference in their entirety for all purposes to the same extent as if each were so individually denoted.

What is claimed is:

1. A method for treating multiple sclerosis in a patient, the method comprising administering to the patient intramuscularly an effective amount of a nucleic acid encoding osteopontin, whereby the nucleic acid is expressed in the patient to produce osteopontin, and the osteopontin induces an immune response wherein the immune response comprises formation of antibodies to osteopontin that reduces the level of osteopontin in the patient, thereby treating multiple sclerosis.

2. The method of claim 1, wherein the nucleic acid is DNA and further comprises a promoter and optionally an enhancer in operable linkage to the segment encoding the osteopontin.

3. The method of claim 2, wherein the promoter is constitutive.

4. The method of claim 2, wherein the promoter is cell-type specific.

5. The method of claim 1, wherein the nucleic acid is DNA.

6. The method of claim 1, wherein the nucleic acid is RNA.

7. The method of claim 1, wherein the subject is a human.

8. The method of claim 1, further comprising monitoring a decrease in the level of osteopontin responsive to the administering step.

9. The method of claim 1, wherein the level of osteopontin is monitored in a cell of the patient selected from the group consisting of a neuron, a macrophage, a vascular endothelial cell, an astrocyte and a microglial cell.

10. The method of claim 1, wherein the disorder and the method further comprises monitoring a decrease in the symptoms of the patient responsive to the administering.

* * * * *

UNITED STATES PATENT AND TRADEMARK OFFICE
CERTIFICATE OF CORRECTION

PATENT NO. : 7,282,490 B2  
APPLICATION NO. : 10/495893  
DATED : October 16, 2007  
INVENTOR(S) : Chabas et al.

Page 1 of 1

It is certified that error appears in the above-identified patent and that said Letters Patent is hereby corrected as shown below:

In The Specification Under Column 1:

* Please replace lines 4-8 with:

-- This invention was made with Government support under contract NS018235 awarded by the National Institutes of Health. The Government has certain rights in this invention. --

Signed and Sealed this  
Fifth Day of April, 2011

David J. Kappos  
*Director of the United States Patent and Trademark Office*